United States Patent [19]
Jacobs et al.

[11] Patent Number: 5,773,267
[45] Date of Patent: Jun. 30, 1998

[54] D29 SHUTTLE PHASMIDS AND USES THEREOF

[75] Inventors: William R. Jacobs, City Island, N.Y.; Graham F. Hatfull, Pittsburgh, Pa.

[73] Assignees: Albert Einstein College of Medicine of Yeshiva University, a Division of Yeshiva University, Bronx, N.Y.; University of Pittsburgh, Pittsburgh, Pa.

[21] Appl. No.: 614,770

[22] Filed: Mar. 7, 1996

Related U.S. Application Data

[63] Continuation-in-part of Ser. No. 247,901, May 23, 1994, which is a continuation-in-part of Ser. No. 57,531, Apr. 29, 1993, abandoned, which is a continuation-in-part of Ser. No. 833,431, Feb. 7, 1992, abandoned.

[51] Int. Cl.$^6$ .............................. C12N 1/21; C12N 15/11; C12N 15/63; C12N 15/74
[52] U.S. Cl. .................................... 435/172.1; 435/252.3; 435/320.1; 536/23.1
[58] Field of Search .................................. 536/22.1, 23.1, 536/23.72; 435/172.1, 172.3, 235.1, 243, 252.3, 253.1, 320.1

[56] References Cited

PUBLICATIONS

Sellers et al. (1970) The effects of ultraviolet irradiation on mycobacteriophages and their infectious DNAs. J. Gen. Virol. 7:233–247, Jun. 1970.
Jacobs et al. (1989) Mycobacteriophage vector systems. Rev. Infect. Dis. 11, Supp. 2:S404–S410, Mar. 1989.
Sambrook et al. (1989) Molecular cloning: a laboratory manual. Cold Spring Harbor Laboratory Press, 13.1–13.102, 1989.

*Primary Examiner*—Nancy Degen
*Assistant Examiner*—Robert Schwartzman
*Attorney, Agent, or Firm*—Amster, Rothstein & Ebenstein

[57] ABSTRACT

The present invention provides a conditional shuttle phasmid constructed by inserting a cosmid into a non-essential region of the D29 mycobacteriophage which is capable of introducing DNA of interest into the chromosome of mycobacteria, especially *M. tuberculosis* complex organisms and other slow growing mycobacteria. The present invention provides a recombinant mycobacterium which expresses a DNA of interest incorporated into its chromosome by a conditional shuttle plasmid containing the DNA of interest. The present invention further provides a mycobacterial auxotrophic mutant and method of generating auxotrophic mutants. Finally, the present invention provides a method of inactivating a mycobacterial virulence gene.

15 Claims, 2 Drawing Sheets

D29 SHUTTLE PHASMIDS AND USES THEREOF

CROSS-REFERENCE TO RELATED APPLICATIONS

This application is a Continuation-in-Part of U.S. application Ser. No. 08/247,901, filed May 23, 1994, which is a Continuation-in-part of U.S. application Ser. No. 08/057,531, filed Apr. 29, 1993, now abandoned, which is a Continuation-in-part of U.S. application Ser. No. 07/833,431, filed Feb. 7, 1992, now abandoned, the contents of which are hereby incorporated herein in their entirety.

BACKGROUND OF THE INVENTION

Tuberculosis (which includes infection caused by *M. tuberculosis, M. bovis*, BCG and *M. africanum*) remains the largest cause of human death in the world from a single infectious disease, and is responsible for one in four avoidable adult deaths in developing countries. In addition, in 1990, there was a 10% increase in the incidence of tuberculosis in the United States.

In the past, infection with drug-sensitive strains of the *M. tuberculosis* complex had been cured with certain antibiotics, including isoniazid, rifampicin, ethionamide and pyrazinamide. However, resistance to isoniazid and other antibiotic drugs has developed in many strains of *M. tuberculosis*. This has resulted in the search for an effective vaccine against *M. tuberculosis*. Further, this has enhanced the need to develop new drugs which are effective against drug-resistant strains of *M. tuberculosis*. It is therefore desirable to develop molecular and genetic tools which can be utilized to understand the pathways involved in invasion, survival and persistence of *M. tuberculosis* and in the development of vaccines and new drugs.

The creation of mutants in *M. tuberculosis* and BCG is of essential importance in the analysis of *M. tuberculosis* and BCG gene function. Auxotrophic mutants have been isolated in *M. smegmatis* by both shuttle mutagenesis and N-methylN'-nitroso-N-nitrosoguanidine treatment followed by isoniazid enrichment. These methods, however, are less effective in the *M. tuberculosis* complex (*M. tuberculosis, M. bovis, M. miroti* and *M. africanum*) due to current difficulties in performing homologous recombination, which is required by the shuttle mutagenesis procedure. Also, the tendency of mycobacteria to clump limits the use of traditional mutagens and makes positive selection advantageous.

Because the creation of mutants in *M. tuberculosis* and BCG is of essential importance in the analysis of gene function, it is desirable to develop effective means and methods for delivering foreign DNA into *M. tuberculosis* and BCG. The insertion of foreign DNA into *M. tuberculosis* and BCG mycobacteria would provide the necessary tools for understanding the mechanisms by which these mycobacteria survive and replicate. In addition, it would provide valuable tools for the development of vaccines and new drugs effective in the treatment of infection caused by *M. tuberculosis* and BCG.

The inventors of the present invention have constructed a class of novel cloning vectors for introducing DNA of interest into *Mycobacterium tuberculosis* complex organisms, i.e., *M. tuberculosis, M. bovis* and Bacille-Calmette-Geurin (BCG), and other slow growing mycobacteria as well as nontuberculosis mycobacteria commonly encountered in biological samples isolated from human subjects. The cloning vector of the present invention is a conditional shuttle phasmid constructed using the D29 mycobacteriophage.

SUMMARY OF THE INVENTION

The present invention provides a purified and isolated nucleic acid encoding D29 mycobacteriophage. The present invention also provides a conditional shuttle phasmid capable of introducing DNA of interest into a mycobacterium and a conditional shuttle phasmid which contains DNA of interest inserted into its genome.

The present invention further provides a recombinant mycobacterium which expresses DNA of interest introduced into its chromosome by a conditional shuttle phasmid containing the DNA of interest.

The present invention also provides an auxotrophic mutant produced by infecting a mycobacterium with a conditional shuttle plasmid containing a transposon such that the transposon is able to incorporate randomly into the chromosome of the mycobacterium thereby generating an auxotrophic mutation and an auxotrophic mutant produced by infecting a mycobacterium with a conditional shuttle plasmid containing a DNA of interest capable of inactivating a particular gene or genes of the mycobacterium.

Finally, the present invention provides a method for generating a library of mutant mycobacteria comprising infecting each member of a wild-type population of mycobacteria with a conditional shuttle phasmid containing a transposon incorporated into its genome at a non-permissive temperature for replication of the conditional shuttle plasmid such that said transposon is able to randomly insert itself into the chromosome of each member of the population of wild-type mycobacteria thereby randomly generating mutations in the mycobacteria as well as a method for inactivating a virulence gene in a mycobacterium comprising infecting the mycobacterium with a conditional shuttle phasmid containing a DNA of interest such that the DNA of interest can become incorporated into the chromosome of the mycobacteria and inactivating the virulence gene.

Additional objects of the present invention will be apparent from the description which follows.

DETAILED DESCRIPTION OF THE INVENTION

Figure 1:
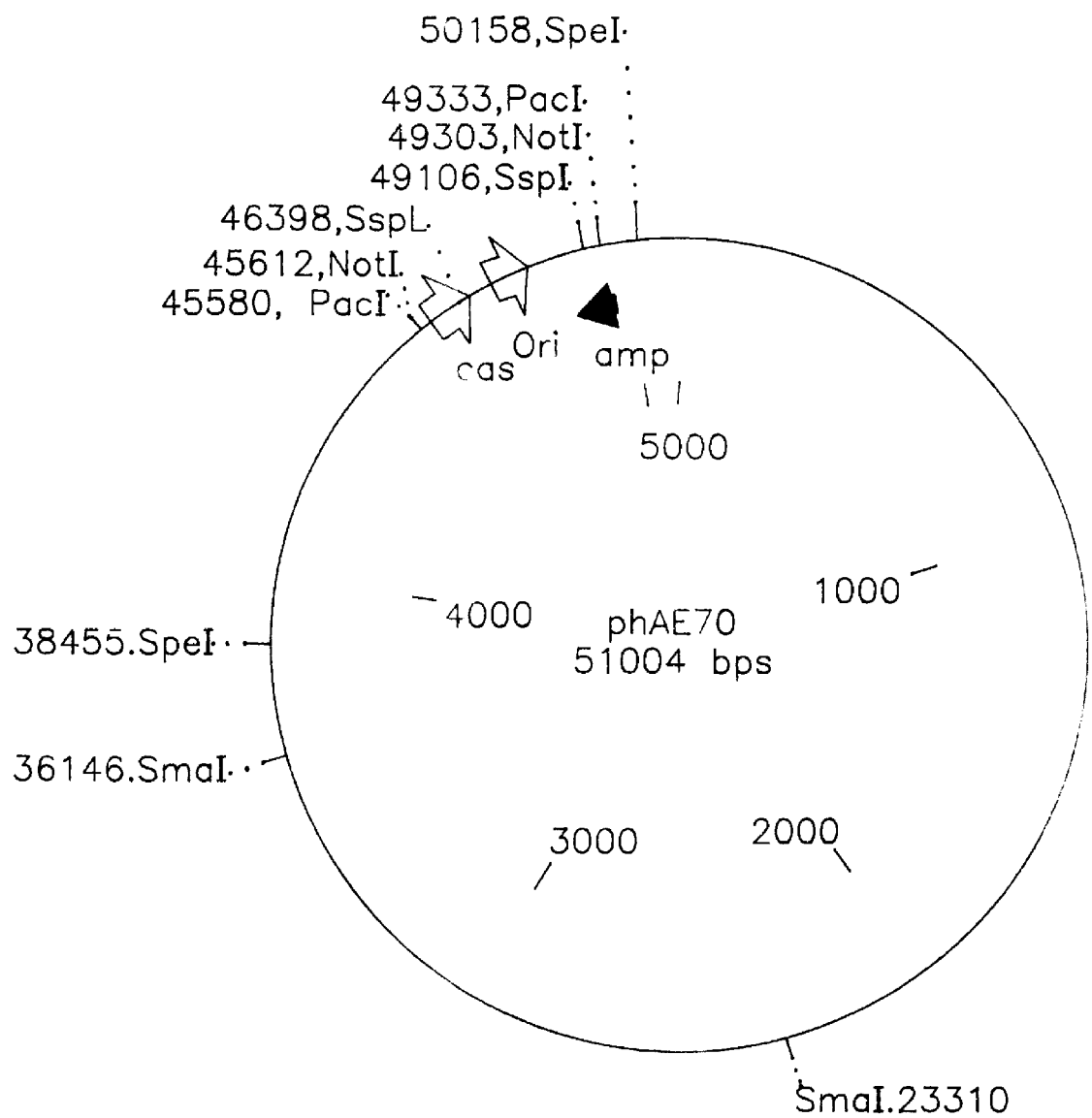
FIG. 1 depicts a schematic representation of the conditional shuttle phasmid phAE70.

The present invention provides a novel class of cloning vectors based on the D29 mycobacteriophage for introducing DNA of interest into mycobacteria. The cloning vectors of the present invention are particularly suited for introducing DNA of interest into *Mycobacterium tuberculosis* complex organisms, i.e., *M. tuberculosis, M. bovis* and Bacille-Calmette-Geurin (BCG), and other slow growing mycobacteria as well as nontuberculosis mycobacteria commonly encountered in biological samples isolated from human subjects, e.g., *M. avium-intracellulare, M.kansasii, M. xenopi, M. scrofulaceum, M. simiae, M. szulgai, M. gordonae, M. gastri, M. smegmatis*, and *M. chelonae*.

The cloning vector of the present invention is a conditional shuttle phasmid which may be produced by exposing the shuttle phasmid formed by inserting a cosmid such as pYUB328 into a non-essential region of the D29 genome and isolating thermosensitive mutants formed thereby, i.e., mutants which are able to produce plaques on *M. smegmatis* at 30° C. but not 37° C.

In the preferred embodiment of the present invention, the cloning vector is the conditional shuttle phasmid designated phAE70 which was deposited under the terms of the Budapest Treaty on Mar. 7, 1996 with the American Type Culture Collection (ATCC), Rockville, Md., and assigned ATCC Accession No. 97468.

The conditional shuttle phasmid of the present invention may introduce DNA of interest into the chromosome of a mycobacterium by homologous recombination, site-specific recombination or nonhomologous recombination. The DNA of interest may be of any origin and may encode proteins or polypeptides of interest including but not limited to antigens, anti-tumor agents, enzymes, lymphokines, pharmacologic agents, immunopotentiators, and reporter molecules of interest.

Antigens include but are not limited to *Mycobacterium leprae* antigens; *M.tuberculosis* antigens; Rickettsea antigens; malaria sporozites and meroziotes; diptherea toxoids; tetanus toxoids; *Clostridium* antigens; *Leishmania* antigens; *Salmonella* antigens; *Borrelia* antigens; *M. africanum* antigens; *M.intracellulare* antigens; *M.avium* antigens; *Treponema* antigens; *Pertussis* antigens; *Schistosoma* antigens; *Filaria* antigens; Herpes virus antigens; influenza and parainfluenza virus antigens; measles virus antigens; mumps virus antigens; hepatitis virus antigens; rabies virus antigens; *Shigella* antigens; *Neisseria* antigens; polio virus antigens; Rift Valley Fever virus antigens; dengue virus antigens; Human Immunodeficiency Virus (HIV) antigens; respiratory syncytial virus (RSV) antigens; snake venom antigens; and *Vibrio cholera* antigens. Enzymes which may be encoded include but are not limited to steroid enzymes.

Anti-tumor agents which may be encoded include but are not limited to interferon-alpha, interferon-beta, or interferon-gamma, and tumor necrosis factor (TNF). Lymphokines which may be encoded include but are not limited to interleukins 1 through 8. Reporter molecules include but are not limited to luciferase (from *Vibrio* or from firefly), beta-galactosidase, beta-glucoronidase, and catechol dehydrogenase. Other peptides or proteins which may be encoded by the DNA of interest include but are not limited to stress proteins, which can be administered to evoke an immune response or to induce tolerance in an autoimmune disease, e.g., rheumatoid arthritis.

The conditional shuttle phasmid of the present invention may also be used to introduce transposons into the chromosome of a mycobacteria. As used herein, the term "transposon" is a general term which encompasses both non-mutated transposons and mutated transposons, i.e., a transposon in which a portion of the nucleotide sequence has been deleted and/or replaced, and/or wherein the transposon contains additional DNA sequences. In general a transposon contains an inverted repeat sequence at the 5' and 3' end, and a gene(s) encoding a transposase enzyme(s) between the inverted repeat sequences. The transposase(s) acts upon the inverted repeat sequences so as to enable the transposon to remove itself from the shuttle phasmid and insert or transpose into the chromosome of the mycobacteria. In some instances, the transposon may also include gene(s) encoding resolvase(s) and/or regulatory protein(s) which regulate transposition.

DNA of interest may be obtained from by a variety of methods, e.g., DNA may be isolated directly from an organism using standard purification procedures or by the cloning and amplification of the DNA of interest using methods known to one skilled in the art of genetic engineering such as PCR. Cloning of the DNA of interest into the conditional shuttle plasmid of the present invention may be accomplished using standard cloning and DNA ligation techniques. For example, the cohesive ends of the shuttle phasmid may be ligated using known ligase enzymes and the resulting molecule digested with a unique restriction endonuclease. Alternatively, a polylinker sequence containing recognition sites for a number of unique restriction enzymes may be inserted into the shuttle phasmid and the polylinker sequences digested with one or more restriction endonucleases in order to generate appropriate restriction sites on the shuttle phasmid to facilitate insertion of the DNA of interest. The use of two unique restriction endonucleases may be preferred for the directional cloning of the DNA of interest.

In addition to the DNA of interest, a selectable marker gene, e.g. a gene which confers antibiotic resistance, may be ligated to the DNA of interest and the resultant molecule ligated into the conditional shuttle phasmid using standard procedures (the conditional shuttle phasmid generally contains antibiotic resistance genes for selection of colonies in *E. coli*). Selectable marker genes which may be included on the DNA of interest are well known in the art and include but are not limited to genes encoding resistance to kanamycin, viomycin, thiostrepton, hygromycin or bleomycin.

The resulting ligated DNA comprising conditional shuttle phasmid DNA, DNA of interest and/or selectable marker DNA is then packaged into bacteriophage lambda heads using a commercially available in vitro packaging mix. *E. coli* is subsequently transduced with the phage colonies containing the ligated DNA are isolated by virtue of their ability to grow in medium containing the antibiotic corresponding to the resistance gene on the cosmid.

The resulting shuttle plasmids are introduced into *M.smegmatis* or other suitable mycobacteria using standard methods known to those skilled in the art such as electroporation. Plaques which contain shuttle phasmids comprising the DNA of interest may be used to infect mycobacteria of interest, e.g., *M. tuberculosis* and BCG.

Infection of mycobacteria such as *M. tuberculosis* with conditional shuttle phasmids containing the DNA of interest is accomplished by mixing the mycobacteria and shuttle phasmid at the non-permissive temperature at a multiplicity which will insure infection of mycobacterium. The calculation of the correct multiplicity is well within the knowledge of one skilled in the art. The phasmid DNA thus enters the mycobacterium but is unable to replicate. In this way the DNA of interest can become integrated into the mycobacterial chromosome and so expressed. Selection of mycobacteria containing the DNA of interest can be detected by virtue of their survival and growth on medium containing the antibiotic corresponding to the selectable markers encoded by the DNA of interest. Alternatively, mycobacteria expressing antigens or other proteins may also be detected by other methods, e.g., use of monoclonal antibodies.

The conditional shuttle plasmids of the present invention may also be used to generate libraries of mutated mycobacteria using conditional shuttle phasmids containing transposons such as Tn567 and mini Tn10 and methods detailed in the Experimental Details Section which follows or conditional shuttle phasmids containing DNA of interest, the expression of which will inactivate a specific mycobacterial gene or genes, e.g., antisense RNA.

Such methods are able to produce auxotrophic mutants, i.e., mutants which require a nutrient or substance not required by the organism from which the mutant was derived, e.g. leucine and other amino acids. Such non-pathogenic mycobacteria may be produced by insertional mutations or deletions causing disruptions of a mycobacterial virulence gene or by the expression of a molecule to block expression of the virulence gene, e.g. by knocking out genes in the mycobacteria which encode virulence factors, enzymes involved in regulation of pathways of the mycobacterium, and the like. Thus the conditional shuttle phasmid of the present invention may be used to generate a library of M.tuberculosis mutants that can be screened for their utility as vaccine strains.

The present invention also relates to methods of vaccinating a host with the recombinant mycobacterium to elicit protective immunity in the host. The recombinant vaccine can be used to produce humoral antibody immunity, cellular immunity (including helper or cytoxic immunity) and/or mucosoal or secretory immunity. In addition, the present invention relates to the use of the antigens expressed by the recombinant cultivable mycobacterium as vaccines or diagnostic reagents as described in WO 90/00594, which is incorporated by reference in its entirety.

Mycobacteria are well known adjuvant properties and so are able to stimulate a subject's immune response to respond to other antigens with great effectiveness. Their adjuvant properties are especially useful in providing immunity against pathogens in cases where cell mediated immunity is critical for resistance. In addition, the mycobacterium stimulates long-term memory or immunity thus a single inoculuum may be used to produce long-term sensitization to protein antigens. The mycobacterial vaccine of the present invention may be used to prime long-lasting T cell memory, which stimulates secondary antibody responses which will neutralize infectious agents or toxins, e.g., tetanus and diptherea toxins, pertusis, malaria, influenza, herpes viruses and snake venoms.

BCG is an especially appropriate vaccine vehicle in that it is the only childhood vaccine currently given at birth, it has a low incidence of adverse effects when given as a vaccine against tuberculosis and it can be used repeatedly in an individual. A further advantage of BCG and mycobacteria in general is the large size of their genomes (approximately $3 \times 10^6$ bp). The large size enables DNA from other sources to be stably incorporated thus making multi-vaccine possible, i.e., a mycobacterium which expresses DNA of interest which encodes antigens from more than one pathogen.

The vaccines or therapeutic agents containing transformed mutated mycobacteria are administered in conjunction with a suitable pharmaceutical carrier. Mineral oil, alum, synthetic polymers are representative examples of suitable carriers. Vehicles for vaccines and therapeutic agents are well known in the art and the selection of a suitable vehicle is well within the skill of one skilled in the art. The selection of a suitable vehicle is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

The shuttle vectors of the present invention can also be used in the diagnosis of infection by mycobacteria. For example, a shuttle phasmid specific for M.tuberculosis or other type of mycobacteria may be ligated to a reporter molecule, e.g., luciferase from Vibrio or of firefly origin; beta-galactosidase; beta-glucoronidase; or catechol dehydrogenase and a strong mycobacterial promoter which controls expression of the reporter molecule-encoding gene. A sample from a subject suspected of suffering from an infection can be tested. The sample is cultured and combined with the specific phage. After a short time, e.g., hours, under appropriate conditions, the sample is assayed using known techniques, to detect the reporter molecule encoded by the DNA in the vector.

Mycobacteria can also be used as a source of a protein encoded by a DNA of interest. The DNA of interest may have a signal sequence added, e.g., from alpha antigen, which is secreted in mycobacteria, beta-galactosidase, agarase or alpha amylase in order to facilitate transport of the protein out of the mycobacterial cell.

The present invention is described in the following Experimental Details Section which is set forth to aid in the understanding of the invention, and should not be construed to limit in any way the scope of the invention as defined in the claims which follow thereafter.

EXPERIMENTAL DETAILS SECTION

I. Development of D29 Conditional Shuttle Plasmid

Shuttle plasmid designated phAE65 was constructed by inserting the Pac1 cosmid pYUB328 into the non-essential region of mycobacteriophage D29 (the entire nucleotide sequence of D29 is shown below) using methods described by Jacobs, et al., Nature, 327:532–536 (1987). D29 infects M. tuberculosis and M. smegmatis.

phAE65 was subjected to hydroxylamine mutagenesis and thermosensitive mutants, designated phAE70 through phAE76, that could plaque M. smegmatis at 30° C. but failed to plaque M. smegmatis at 37° C. were isolated. Mutations in early phage infection functions were screened for by selecting phages that failed to kill M. smegmatis at the non-permissive temperature. FIG. 1 depicts a schematic representation of the conditional shuttle phasmid phAE70 which was deposited with the ATCC, Rockville, Md., on Mar. 7, 1996 and assigned ATTCC Accession No. 97468.

A minimally sized cosmid, pYUB552, whose size of 2.7 kb after packaging made it possible to clone an additional 4.4 kb of DNA into the vector was cloned into phAE70. The cosmid portion of the conditional shuttle phasmids exemplified by phAE70 may be completely excised by digestion of the conditional shuttle phasmid with Pac1.

II. Construction of Conditional Shuttle Phasmids Containing a Transposon

Transposons Tn5367 and mini Tn10 d aph were cloned into pYUB552 using standard methods to generate pYUB553 and pYUB554, respectively. Using standard cosmid cloning technology in E. coli cosmid pYUB328 was replaced by the cosmids pYUB553 (containing Tn5367) and pYUB554 (containing mini Tn10 d aph) to generate shuttle plasmids phAE77 and phAE78, respectively. Titers of D29-packaged shuttle phasmids in excess of $5 \times 10^{10}$ were prepared following transfection of M. smegmatis at 30° C.

III. Infection of mc²155 With Conditional Shuttle Phasmids containing Transposons M. smegmatis mc²155 cells were infected at a multiplicity of 10 with phAE77 and phAE78 at the non-permissive temperature. A multiplicity of infection of 10 was used in order to ensure that every cell in the population was infected with a conditional shuttle phasmid. Infection of the cells occurred at the non-permissive temperature. Therefore the the phasmids were able to enter the cell but were unable to replicate.

Figure 2:
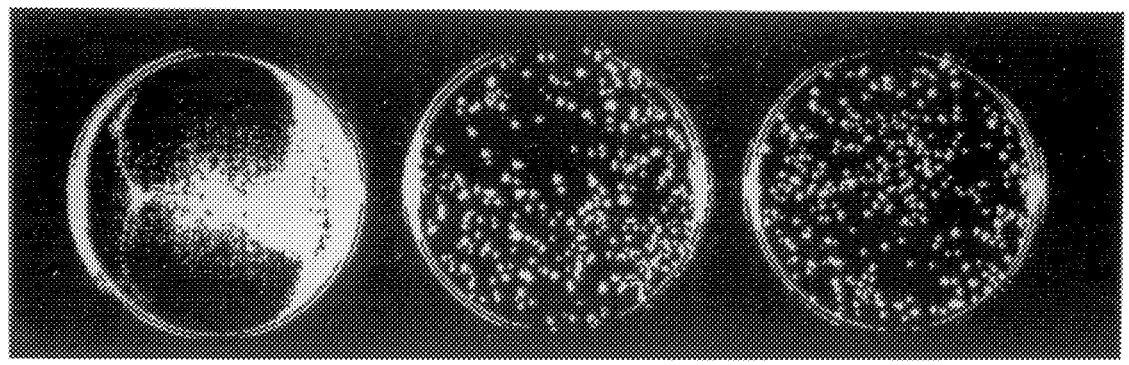
FIG. 2 depicts the effect of infection of mc$^2$155 cells with phAE78. phAE78 contains the transposon min Tn10. Kanamycin-resistant colonies can be observed on the plates on the left of FIG. 2. The control consisting of mc$^2$155 cells shows no kamamycin-resistant colonies.

For *M. smegmatis* greater than $10^4$ kanamycin-resistant colonies per $10^9$ mc$^2$155 cells were observed using phAE78 (see FIG. 2) and greater than 1000 kanamycin-resistant colonies per 108 cells were observed with BCG cells and phAE77. In both cases control plates consisting of cells alone yielded no kanamycin-resistant colonies (see FIG. 2). Since the gene for kanamycin-resistance is carried on the transposon it was concluded that the kanamycin-resistant colonies are the result of transpositions.

Although the invention herein has been described with reference to particular embodiments, it is to be understood that these embodiments are merely illustrative of various aspects of the invention. Thus it is to be understood that numerous modifications may be made in the illustrative embodiments and other arrangements may be devised without departing from the spirit and scope of the invention in the appended claims.

---

What is claimed:

1. A purified and isolated nucleic acid encoding D29 mycobacteriophage having the sequence of SEQ ID NO: 1.

2. A shuttle phasmid comprising a D29 mycobacteriophage which contains an *E. coli bacteriophage lambda cosmid* inserted into a non-essential region of said D29 mycobacteriophage.

3. The shuttle phasmid of claim 2 wherein said cosmid is excised by PacI.

4. The shuttle phasmid of claim 2, deposited under ATCC Accession No. 97468 and designated phAE70.

5. The shuttle phasmid of claim 2 further comprising a DNA of interest inserted into said *E. coli bacteriophage lambda cosmid*.

6. The shuttle phasmid of claim 3, that replicates at a temperature of 30° C., but not at 37° C.

7. The shuttle phasmid of claim 5, wherein said DNA of interest is a transposon.

8. The shuttle phasmid of claim 5, wherein said DNA of interest encodes a protein or polypeptide selected from the group consisting of: antigens, enzymes, lymphokines, immunopotentiators, selectable markers and reporter molecules.

9. A recombinant mycobacterium which expresses a DNA of interest introduced into its chromosome by the shuttle phasmid of claim 5.

10. An auxotrophic mutant produced by infecting a mycobacterium with the shuttle phasmid of claim 7, such that said transposon incorporates randomly or site-specifically into the genome of said mycobacterium thereby generating an auxotrophic mutant.

11. A method for producing a mutant mycobacterium comprising infecting a mycobacterium with the shuttle phasmid of claim 9 under conditions such that said transposon randomly or site-specifically inserts itself into the genome of said mycobacterium, thereby generating a mutation in said mycobacterium.

12. The recombinant mycobacterium of claim 9, wherein said DNA of interest encodes one or more proteins or polypeptides selected from the group consisting of: antigens, enzymes, lymphokines, immunopotentiators, selectable markers and reporter molecules.

13. The recombinant mycobacterium of claim 9, wherein said DNA of interest is a transposon.

14. The recombinant mycobacterium of claim 9, which is *M. tuberculosis, M. bovis*, BCG, or *M. avium*.

15. The auxotrophic mutant of claim 10 which is *M. tuberculosis, M. bovis*, BCG, or *M. avium*.

\* \* \* \* \*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 49272
        ( B ) TYPE: NUCLEIC ACID
        ( C ) STRANDEDNESS: DOUBLE
        ( D ) TOPOLOGY: LINEAR ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: MYCOBACTERIOPHAGE
        ( B ) INDIVIDUAL ISOLATE: D29

( x i ) SEQUENCE DESCRIPTION: SEQ ID NO: 1:

```
GGTCGGTTAT  GCGGCCGAGC  CATCCTGTAC  GGGTTTCCAA  GCCGATCAGA  AGCACGGGCC    60
GACGCTAGAG  CGCCTCGCCC  AGGCGCTGTG  AGCCACCAGG  AGCCACGAAC  TCGCGACCCA   120
CGGGGAGTTA  TACCCCCGGA  ATCGGCTACG  GGCCATACAG  GCCCGGTATC  TGTCAAGGTG   180
ATCTACGCCA  CTCCGTGGGG  TGGCTGTCAA  ACGCAGACTC  CTTCCCTATT  AATGAGGGGC   240
TGAAGGCCCC  TCCTAAGAGC  CGCTTCAGGC  GGCTCGCTAA  GAGCGCCTTT  CGGGCGCTCC   300
TGAGTAATAA  CCGGCCCAAC  AAGGGCCGGG  GAATTGATCC  GGCAACCGCC  GGATCTAGCG   360
CCGCGCCTGA  AGCGCGGCTT  ATTGAAGGGG  TGACGCAACC  GTGTACGGCA  CTCGTTCGAG   420
TGCGTACTGG  AGCACTCAAC  CGGGGAAGTT  CGACGTTCTC  AACCTTCGGA  TGACGTTCCC   480
AAGCTCATCC  GCGTACGAGA  TCCCCGATCT  GCGGCCGACA  ACCTACGTTC  CGGCCAACCT   540
CGCGGCCTGG  AACATGCCGC  GACATCGCGA  ATACGCCGCC  GTTTCGGGCG  GCGCACTGCA   600
CTTCTTCCTT  GACGACTACC  GATTCGAGAC  CGTCTGGTCG  AGCCCGGAGC  GCCTTCTCCC   660
CCGCGTGCAA  GCGGTTGGAG  CTGCTCTGAC  GCCCGATTTC  AGCCTCTGGC  GGGACATGCC   720
ACGGGCCGCA  GCGGTCTGGA  ACGTCTACCG  CAGCCGCTGG  TGCGGCGCGT  ACTGGCAGTC   780
GCAAGGGATC  GAGGTGCTCC  CAACCGCGTG  CTGGGCGACC  CCAGACACGT  TCGACTTCTG   840
CTTCGACGGG  ATCCCGGAGG  GGGCCACGGT  CGCGATCAGC  TCGATGGGCA  TCCGCTCCTC   900
GAAGGTCGAC  CAGGCGCTTT  TCCGCGCTGG  CCTCCAGGAA  CTCCTCGATC  GCAAGCAACC   960
GCGACTGCTG  CTGGCCTACG  GCCGGCTGCG  GTACTGCGAC  GACATGAACC  TTCCCGAGGT  1020
CAAGGAGTAC  CCGACCTACT  GGGACAGACG  ACGAAAGCAG  GTATCCGACG  CATGGGCGGA  1080
AGAGGATCCG  CCGGTAGCGG  CGGTGCCCCT  GGAACCCGAG  GACGCAACAG  CACCCGGCAA  1140
GGAGCCGGGG  CAGGCGGCGT  GGGTGGACTT  GGAGGCGGCG  GTGGAGCCGC  CGGAAGCGGC  1200
```

| | | | | | |
|---|---|---|---|---|---|
| CGGGGCGGTT | TAGGCACCGG | CAACGCAGGC | ACCGGTGGTG | TACTCGGTGG | CGGCGGCAGC | 1260 |
| GGAGCTGGCG | GCGGGTTCGG | TGGTTCGACC | GGCAGCCAGA | CGCCAGACTG | GACCTACAAC | 1320 |
| AGCCCGATGG | ACCCCGCGCA | GAAGCGTGCG | GCGTTCAACG | CGCTGGCGGT | CGCCGCCCGC | 1380 |
| GACCAGCACT | CACCGTCGGA | TGCCAAGCGC | ATAGCGAAGA | GGGACCAGAT | GCTCGGATAC | 1440 |
| GTTCGAGGGC | CGTGGGAGCA | GTTGGAGGAC | GACGACTCCA | CCCGCTACGA | CACCCTGAAG | 1500 |
| CAGGCGATGG | ACGACGCCAT | GTCCAAGATC | CTGAGCCAGG | CGCAGGTGGT | CCACCGCACG | 1560 |
| AAGCACCTGG | ACAAGCTCCT | GGACTCGGGC | CGGATCTCCT | CGCTGTTCGA | GGTCGGCTTC | 1620 |
| TCGGCCGGTG | GCGACACCCC | CGGTCAGCGC | GCTCTGTACG | AGGAGGCGTG | GTTCGGCAAG | 1680 |
| GGCCACGTCC | CGCCGGTCTA | CTCCGCGCTG | GAGTTCGACG | GCGTCAAGCC | CAAGGGCATG | 1740 |
| AGCATGTACG | GCAGCACCAA | GCTCTACCTC | AAGCCCGAGG | TGCGTGACCG | GGTCACTGTG | 1800 |
| ACCATCGGCG | ACTCGCTGAT | GTCGAGCGAC | AGCGTGTTCC | CCGGAAAGCC | GGGTGACGGC | 1860 |
| CTCGGCCTGC | GGGCGAATCC | GAATGCGATC | AAGAACCTCG | TAGACCCGAA | TAAGTCTCGC | 1920 |
| GAAGAGAACA | TGCAGGCGAT | CTACGAGAGC | TTCAAGAAAT | ACGCCGAATC | GAATTTCATC | 1980 |
| GAATCGCAAA | TTCACGACGG | CGTTATTCTC | GAAGACATCG | AGAAGGTTGT | ATTCACTCAG | 2040 |
| CCGCCCAGCT | CTTTCCTGAC | TGATAAACTG | GACAAGCTCG | GAATACCGTG | GGAGGTGGAA | 2100 |
| TCGTAATGGC | GCTGATGCAA | GCGACACACA | CCATCGAGGG | CTTTCTCGCG | GTCGAAACGC | 2160 |
| ACCCGAGGGC | GTTCGTGGCC | GAGAATGGCC | ACGTGATCAC | CCGCCTCTCG | GCCACCAAGT | 2220 |
| GGGGTGGCTG | GGAGGGCCTG | GAGATCCTTG | AGTACTCGGG | TGACGGCCAG | GTCGAGGTCA | 2280 |
| GCGACGAGCA | GTTGGCTGAG | GCGGAACACG | CCAGCCAGAT | CGAAGCACAG | ATCATCGCGG | 2340 |
| AGGCAGCCGC | AGAGTGAGTT | GGGCCGGCTC | GAAGCGTCGG | CAAGAACTAC | CGGAGGACTG | 2400 |
| GGAGCTGAAT | TACCGGCTCC | CGGTCCTTTC | TGCTGCCGGG | TGGCTGTGTG | AGGTCGACGG | 2460 |
| CCCCGGCTGC | GTCCGGGCTG | CCACCGACGT | AGACCACAAG | AAGCCAGGGA | ACGACCACTC | 2520 |
| GCGGTCTAAC | CTGCAAGCGA | TCTGCCGTGT | CTGCCACGGC | AAGAAGTCAG | CCGCTGAGGG | 2580 |
| CGTAGCCCGA | CGGCGGGAAC | TCAAGGCCCG | GAGGAAGCGA | CCAGAACAAC | GCCACCCTGG | 2640 |
| GCGTCGTTAA | GCGGGCCAGG | TGCCTGCTCC | ACCCAGGAGG | TGACTGTGGG | CACACGTGGC | 2700 |
| CCCATCGGAA | AGCGCGACGA | AGAACGCGTT | CGTCGCAACA | CCCCGGAGAA | CCCGACCGAA | 2760 |
| ACGATCTCGA | TGATCGGGAC | GGTGGAGATC | CCGGAACTCG | GCGACATGAG | CTACATGGGC | 2820 |
| GAGACCCATC | CGCTCATCGA | AGAGATGTAC | GACGCGATCA | AGCAATCGGC | AGCCGTGAAG | 2880 |
| TTCTACGAAC | CGACCGACTG | GCAGTTCGCT | CGCCTCGCTC | TCTACACACT | GAACCAAGAA | 2940 |
| CTCATCGCGG | CCAAGCACCA | GGGCAAGCCC | ATCGGTGCGA | TGAAGCTGAC | CGCGATCAAC | 3000 |
| CAGATGCTCT | CCGCACTGCT | GCTGACCGAA | GGCGACCGGC | GACGGGTCCG | CCTGGAGATC | 3060 |
| GAGCGGGCAC | CCGCCGACCC | GACCGGCGGG | AAGGTCGTTG | ACGTGACCGA | CGTGCTCAAG | 3120 |
| CAGCGCCTCG | CCAAGGCGAG | CGGCGGGGGG | TGATGGTCCC | CCTGGCGGGG | TTCTGAGCGG | 3180 |
| TTGCCGCTAC | CGACTGCTCC | CCCGCCGGGG | GTTGACCCTC | GAACTTGAA | AGGATCCGCA | 3240 |
| TGGCCGACCT | CGGCAACCCG | TTCGACCTGG | AGATGCTCTG | CCTGGTCACC | GGCCGCGACT | 3300 |
| TCCGCTGGTC | GATCCCCCAC | CTCGACCCGG | TCACCAAGCA | GCCCACCCCC | TGGCCTGCGG | 3360 |
| GCGACCTGTT | CCTCGAACTG | GAGACCGGCG | GCGAGCACAA | CGCGCTGCAC | CAGGTGTACA | 3420 |
| TCACCGGGGC | CACAGGTGGC | ACGTACACCC | TGAACCTCAA | CGGCACCGAC | ACCCCGGCCA | 3480 |
| TCGACTACAA | CGACGTGTCC | GAGAACCCGC | AGGGTCTGGC | CGGTGACATC | CAGGACGCCA | 3540 |
| TCGACGCGGC | GCTCGGGGCC | GGTAACGGCC | TGGTGCATCC | GGTCTCGCTG | TTCCCCGCGT | 3600 |

```
GGACGCTGAA CTTCAACCTG AACGCCCGCA AGCCGCTGAC CGAGCAGTTG GTCAACACGA      3660

TCAACAAGGC CACGAACGAC TTCTTCGATG CGTTCGACCA GCTCCTCGGG GTCGACGTGG      3720

AGATGACGGT CACCGACACC CTGAACTTCC AGCTCAAGGT GACCTCGCGG CGCTCGTTCG      3780

ATGAGGTCGG CGTCGTCACC TTCGCGGTCG GCGTGACCTC GACGGCGGTC AAGAACTTCT      3840

TCAACGGCTT CTCCGGGCTG ATCGGCGCGG TGAACACCGT CAACGTCGAC TTCTACTGGA      3900

ACCGGACCTA CGACATCGAG TTCGTCGGCG AGCTGGCCGA GACGCCGGTA CCCGCCTCCA      3960

CGGCGAACGC GGCCGGTCTC ACGGGCACCT CGAAGGCCAT CACCGTCTCG GTGGTCGAGC      4020

CAGGCAAGGA CCGCCTGACC ATCTGGCCGT TCACGATCGA CGGCGTGACC GCCTCGATCA      4080

AGGTCGAGTC CGAAGAGGCC GACAAGATCC GAACCGCTG CCGCTGGCAG TTGGTTCATC       4140

TGCCGACCGG CGAAGCGGCC GGCGGTGACC CCAAACAACT CGGCGTCGTC TACCGGCAAC      4200

CCCGGTAGGC GCACCACTGA CGTGTAGCTC AATGGCAGAG CATCCGGCTG TTAACCGGAC      4260

GGTTGAAGGT TCGAGTCCTT CCTCGTCAGC CAAGCGGGCG GTTCCCAGA GCGTGGGGAG       4320

CCCCCGCACC AAGTACACGT AGCTCAATTG GTAGAGCAGC GGTCTCCAAA GCCGCCGGTT      4380

CCAGGTTCGA CTCCTGGCGT GTATGCCACC ACCCTTCCCC GTTCGTCTAA TCGGTAAGAC      4440

GCCTGGCTCT GGACCAGGTA ATTGAGGTTC GAGTCCTTGG CGGGGAGCAC CCACCCAGTT     4500

CCCTTGTGGG GCTGGGTCTT TCGGTCCCTT GGAGTAGCGG ATAACTCACC TGGCCCTCAC      4560

CCAGAAGATC GCGGGTTCGA ATCCCGCAGG GACTACAAAC GCGAGATACC CAAGCGGCAA     4620

CGGGATCTGA CTGTAAATCA GACGCTTCGG CTTCGCAGGT TCGAGTCCTG CTCTCGCGAC      4680

TTGACAGCCA CCACGAAAGG AACCCATGAC GCTCATAGTC ACACGCGACC ACGCGCAGTG      4740

GGTCCACGAC ATGTGCCGCG CTCGCGCTGG CAACAGGTAC GGCTACGGCG GGGCGTTCAC      4800

ACTCAACCCC CGAGACACCA CCGACTGCTC GGGTCTGGTT CTGCAGACGG CAGCCTGGTA     4860

CGGCGGTCGG AAGGACTGGA TCGGAAACCG GTACGGCTCG ACTGAGAGCT TCCGGCTCGA      4920

CCACAAGATC GTCTACGACC TCGGGTTCAG GCGACTCCCT CCGGGAGGCG TTGCGGCCCT     4980

GGGATTCACC CCGGTCATGC TCGTCGGGCT CCAGCACGGC GGCGGGGGCC GGTACTCGCA     5040

CACCGCTTGC ACGCTGATGA CGATGGACAT CCCCGGTGGC CCGGTGAAGG TCTCGCAACG     5100

AGGCGTCGAC TGGGAGTCCC GAGGAGAAGT CAACGGCGTG GGGGTGTTCC TCTACGACGG     5160

CGCACGCGCC TGGAACGACC CGCTCTTCCA CGACTTCTGG TACCTGGACG CGAAGCTTGA      5220

AGACGGCCCG ACGCAGAGTG TCGACGCTGC CGAAATCCTC GCTCGCGCAA CGGGTCTCGC     5280

GTACAACCGA GCGGTAGCAC TGCTGCCGGC CGTGCGTGAC GGCCTCATCC AGGCCGACTG     5340

CACCAACCCG AATCGCATCG CGATGTGGCT CGCCCAGATC GGCCATGAGT CAGACGATTT      5400

CAAGGCCACT GCGGAGTACG CCAGCGGGGA CGCCTACGAC ACCCGAACCG ACCTCGGCAA     5460

CACCCCGGAG GTCGACGGAG ACGGTCGGCT CTACAAGGGC CGGTCCTGGA TCATGATCAC     5520

GGGCAAGGAC AACTACCGGG ACTTCTCCCG GTGGGCTCAC GGCAGGGGCC TGGTCCCCAC      5580

GCCCGACTAC TTCGTGGTTC ACCCGCTGGA GCTGTCGGAG CTGCGCTGGG CAGGCATCGG     5640

TGCCGCCTGG TACTGGACCG TCGAGCGCCC AGACATCAAC GCACTCAGCG ACCGCCGCGA     5700

CCTCGAAACG GTCACGCGCC GGATCAACGG CGGGCTCACC AACCTCGATG ACCGCCGACG     5760

CCGGTACAAC CTGGCCCTCG CTGTGGGCGA CCAACTACTG ACTCTGATCG GAGATGACGA     5820

CGAATTGGCT GATCCAACGA TTCAGCGGTT CATCCGCGAG ATCCACGGGG CGCTGTTCAA     5880

CACCGTCGTG ACGCAGTCCC CCTACGGCGA CCCGCAGAAC CCGGACGGCT CGGAGCCCCG     5940

GAGCAACCTC TGGCAGCTCC ATGAGCTGAT CAAGAACGGC GACGGCATGG GGCACGCCCG     6000
```

```
CTACGTCGAG GAATCGGCGC GAGCCGGTGA CCTCCGCGAG CTGGAGCGAG TTGTCCGCGC    6060
CGCCAAGGGA CTTGGTAGGG ATCGCTCCCC CGAGTTCATC GCACGCGCTC GGAACGTGCT    6120
GGCCCAGATC GAGGCAGCCA ACCCCGAGTA CCTACAGGCG TACATCGCCA GGAATGGAGC    6180
CCTATGAGCC CCAAGATCCG TGAAACGCTC TACTACGTCG GCACTCTCGT CCCCGGCATC    6240
CTGGGCATCG CCCTGATCTG GGGCGGGATC GACGCGGGCG CAGCCGCGAA CATCGGCGAC    6300
ATCGTCGCTG GCGCTCTCAA CCTGGTCGGC GCAGCCGCAC CGGCCACGGC CGCTGTCAAG    6360
GTCAACCAGC AGCGCAAGGA TGGCACGCTG ACCACCTCCC CGGTGGATCA GGTCACCAGG    6420
GGCGTCGAGC AGGTGCTCGC GGCCAAGCAG AACGCTGAGG CTGAGGTCGA GCGCGTCAAG    6480
CAGGCTCTGG AGTCCGCTGT CAACGGCGCG GTCCCCAGC TCGGCCCGCT GGCCAGCCAG    6540
ATCCTCAACG GCATCCAACC GGCCTACAGC CAGCCGTTCG ACCCGCACAC GCAGCCCTGG    6600
AACCGATGAG CAAGCCCTGG CTGTTCACCG TTCACGGCAC GGGCCAGCCC GATCCCCTCG    6660
GGCCTGGCCT GCCTGCCGAT ACGGCACGCG ACGTACTTGA CATCTACCGG TGGCAGCCCA    6720
TCGGCAACTA CCCCGCTGCG GCCTTCCCGA TGTGGCCGTC GGTCGAGAAG GGTGTCGCCG    6780
AGCTGATCCT GCAGATCGAG CTGAAGCTGG ACGCGGACCC CTACGCGGAC TTCGCGATGG    6840
CGGGTTACTC GCAGGGAGCC ATCGTGGTTG GCCAGGTGCT CAAGCACCAC ATCCTGCCTC    6900
CGACGGGCAG GCTCCACAGG TTCCTGCACC GGCTCAAGAA GGTCATCTTC TGGGGTAATC    6960
CCATGCGGCA GAAGGGCTTT GCCCACTCTG ACGAGTGGAT CCACCCGGTC GCTGCCCCTG    7020
ACACCCTCGG AATCCTCGAG GACCGGCTCG AAAACCTGGA GCAGTACGGC TTCGAGGTCC    7080
GCGACTACGC CCACGACGGT GACATGTACG CCTCCATCAA AGAGGACGAC CTGCACGAAT    7140
ACGAGGTCGC CATCGGCCGG ATCGTGATGA AGGCCAGCGG CTTCATCGGT GGCCGGGACT    7200
CCGTGGTAGC CCAGCTCATC GAGCTTGGCC AGCGTCCGAT CACCGAGGGA ATTGCGTTGG    7260
CGGGAGCCAT CATCGACGCC CTCACGTTCT TCGCCCGCTC TCGTATGGGC GACAAGTGGC    7320
CGCACCTCTA CAACCGCTAC CCGGCGGTCG AGTTCCTACG ACAGATCTGA GAAAGGAGGC    7380
GGGGTGAGCC TCGACAATCA CCACCCGGAG CTTGCCCCGT CTCCGCCTCA CATTATCGGC    7440
CCGTCATGGC AGAAGACGGT CGACGGAGAT TGGCATCTGC CGGATCCCAA GATGACCCTT    7500
GGATGGGGCG TCTTGAAATG GCTGTCGGAG TACGTCAATA CCCCTGGGGG ACATGACGAT    7560
CCGAACCGCC TCAAGGTTTT GATCTCGCTG TCCGAAGCAG GACTGCTTGA GAACGAGAAC    7620
ATGTTCATCC CCACCGACGA GCAGGTACGC CTGGTCCTCT GGTGGTACGC CGTAGACGAG    7680
AAGGGCCAGT ACGTCTACCG CGAAGGCGTG ATCCGGCGGC TCAAGGGATG GGGCAAAGAC    7740
CCGTTCACCG CCGCGCTGTG TCTCGCCGAA CTCTGTGGCC CAGTAGCATT CTCACACTTC    7800
GATGAGACCG GTCAGGCGAT CGGCAAGCCG CGCCCCGCAG CGTGGATCAC CGTCGCGGCC    7860
GTCAGCCAGG ACCAGACGAA GAACACGTTC TCGCTGTTCC CGGTGATGAT CAGCAAGAAG    7920
CTGAAGACCG AGTACGGACT CGATGTCAAC CGGTTCATCA TCTACTCCGC GGCCGGTGGC    7980
CGCATCGAGG CAGCAACCTC CTCACCAGCA TCGATGGAGG GTAACCGCCC GACGTTCGTC    8040
GTTCAGAACG AGACCCAGTG GTGGGGCCAG GGGCCTGACG GCAAGGCCAA CGAAGGCCAC    8100
GCGATGGCCG AGGTCATCGA AGGCAACATG ACCAAGGTCG AGGGCTCTCG CACCCTGTCG    8160
ATCTGCAACG CCCACATCCC CGGCACCGAG ACGGTCGCCG AGAAGGCGTA CGTCGAGTGG    8220
CAGGACGTGC AGTCCGGGAA GTCCGTCGAC ACAGGCATGA TGTACGACGC TCTCGAAGCG    8280
CCGGCCGACA CCCCGATCTC CGAGATCCCT TCTGAGAAGG AGAATCCCGA CGGGTTCCGG    8340
GAGGGCATCG AGAAGCTCCG CGAGGGGCTG TTGATCGCCC GAGGCGACTC CACGTGGCTG    8400
```

-continued

| | | | | | |
|---|---|---|---|---|---|
| CCGATTGACG | ACATCATCAA | GTCGATCCTG | TCGACCAAGA | ACTCGATCAC | CGAGTCACGG | 8460
| CGCAAGTTCC | TCAACCAGGT | CAACGCGGCC | GAGGACTCCT | GGCTGTCACC | GCAGGAGTGG | 8520
| AACCGCTGCT | TCGCCGACCC | GGACAAGTAC | CTCGACAAGA | TGGGCTTCGA | GCTGGCTCCG | 8580
| CTGGACCGGG | GCCAGAAGAT | CACCCTCGGG | TTCGACGGGT | CCAAGTCCAA | CGACTGGACG | 8640
| GCTCTGGTCG | GCTGCCGGGT | CTCCGACGGC | CTGCTGTTCG | TCATCGACAT | CTGGGATCCC | 8700
| CAGAAGTACG | GCGGCGAAGT | GCCCCGCGAG | TTCGTGGACG | CTGCAGTGCA | TTCCGCGTTC | 8760
| TCCCGGTACG | ACGTGGTCGC | GTTCCGCGCC | GACGTGAAGG | AGTTCGAGGC | ATACGTCGAC | 8820
| TCCTGGGGCC | GGACCTACAA | GAAGAAGCTC | AAGGTCAACG | CCAGCCCGAA | CAACCCGGTG | 8880
| GCGTTCGACA | TGCGCGGTCA | GCAGAAGCGA | TTCGCGTTCG | ACTGTGAGCG | CCTGGAGGAC | 8940
| GCGGTCCTCG | AAGGCGAGGT | CTGGCACGAC | GGCAACCCGG | TGCTTCGGCA | GCACGTCCTG | 9000
| AACGCCAAAC | GACACCCAAC | TACCTACGAC | GCCATCGCGA | TTCGCAAGGT | CACCAAGGAC | 9060
| TCCAGCAAGA | AGATCGACGC | TGCAGTCTGC | GCTGTCCTCG | CGTTCGGGGC | GAGACAGGAC | 9120
| TACCTCATGA | GCAAGAAGGC | CCGCACGGGC | CGGGTGGTGG | CCGTCCGATG | ACAGCCCGC | 9180
| TCCCCGGACA | GGAGGAGATC | GCTGATCCGG | CGATCGCCCG | AGACGAGATG | GTCTCGGCGT | 9240
| TCGAGGACCA | GAACCAGAAC | CTCCGATCGA | ACACCAGCTA | CTACGAGGCT | GAGCGCCGAC | 9300
| CAGAGGCCAT | CGGCGTCACG | GTGCCCGTCC | AGATGCAGTC | ACTGCTGGCT | CACGTCGGAT | 9360
| ACCCCCGGCT | GTACGTCGAC | TCGATCGCAG | AGCGACAGGC | TGTCGAGGGT | TTCCGGCTCG | 9420
| GGGACGCCGA | CGAGGCGGAC | GAAGAGCTGT | GGCAGTGGTG | GCAGGCGAAC | AACCTCGACA | 9480
| TCGAGGCCCC | GCTGGGCTAC | ACCGACGCTT | ACGTCCACGG | CCGGTCGTAC | ATCACGATCA | 9540
| GCCGCCCTGA | CCCCCAGATC | GACCTTGGGT | GGGATCCGAA | CGTCCCGCTG | ATCCGGGTGG | 9600
| AGCCCCGAC | GCGCATGTAC | GCCGAGATCG | ATCCTCGGAT | CGGTCGGCCG | GCCAAGGCAA | 9660
| TTCGTGTCGC | GTACGACGCA | GAGGGCAACG | AGATCCAGGC | TGCCACGCTC | TACACCCCCA | 9720
| ACGAGACGTT | CGGGTGGTTC | CGGGCCGAAG | GCGAGTGGGT | GGAGTGGTTT | AGCGACCCCC | 9780
| ACGGGCTCGG | CGCGGTCCCG | GTGGTCCCGC | TTCCGAACCG | GACCCGGCTC | TCGGACCTGT | 9840
| ACGGCACCTC | TGAGATCACC | CCGGAGCTTC | GGTCGATGAC | CGACGCGGCG | GCTCGAATCC | 9900
| TGATGCTGAT | GCAGGCGACT | GCGGAGCTGA | TGGGCGTGCC | CCAGCGACTG | ATCTTCGGCA | 9960
| TCAAGCCCGA | AGAGATCGGC | GTAGACCCCG | AGACCGGACA | GACGCTGTTC | GACGCGTACC | 10020
| TCGCCCGCAT | CCTGGCGTTC | GAGGACGCCG | AAGGCAAGAT | CCAGCAGTTC | TCGGCAGCCG | 10080
| AGCTGGCCAA | CTTCACCAAC | GCACTCGATC | AGATCGCCAA | ACAGGTCGCT | GCGTACACGG | 10140
| GACTCCCTCC | CCAGTACCTG | AGTACCGCCG | CTGACAATCC | GGCCTCCGCT | GAGGCCATCA | 10200
| GGGCCGCAGA | GAGCCGCCTG | ATCAAGAAGG | TCGAGCGGAA | GAACGCGATC | TTCGGCGGTG | 10260
| CGTGGGAAGA | GGCGATGCGC | CTGGCCTACC | GGCTGATGAA | GGGTGGCGAC | GTTCCCCCGG | 10320
| ACATGCTCCG | CATGGAGACG | GTCTGGCGTG | ACCCGAGCAC | CCCGACGTAC | GCCGCGAAGG | 10380
| CTGACGCCGC | CACGAAGCTC | TATGGCAACG | GCCAGGGCGT | GATCCCGCGT | GAGCGGGCTC | 10440
| GCAAGGACAT | GGGCTACTCC | ATCGCCGAGC | GCGAGGAGAT | GCGCCGCTGG | GACGAGGAAG | 10500
| AGGCCGCGAT | GGGCCTCGGC | CTGCTGGGCA | CGATGGTCGA | CGCCGACCCG | ACGGTCCAG | 10560
| GCTCCCCCAA | CCCCACGCCA | GCTCCCAAGC | CACAACCGGC | CATCGAAGGG | GGTGATTCCG | 10620
| CCTGACGCCT | GAGCAGTATG | CAGCGGCCCA | GGCCGTGATC | ACTGCGGGGC | TCGCCGGGTA | 10680
| CGTCCAGCGG | TTCGCCAGTC | TCTTCATCCG | CCCAGCTCTC | TCCATCGCGG | AGTGGCTGCG | 10740
| GCTACTGCAG | GTGTTGTTCC | CAGAGGTCCA | GCGTCGGTAT | GCGGAAGCTG | CCGACCTGGG | 10800

```
CCGGGACTTC  TACGACTCCC  AGCGCAGACT  CCACCACCCG  GAGCTTCCCC  GCAACGAGAG   10860
GTTGCGGAGC  GACCTCCAGT  GGGAGTGGTT  CGTCAGGAAC  ATGGAGCCCG  CACGAAAGGG   10920
GTTGTCGCAG  GCCGACTCTC  CTCAAGCTGC  GGTCACCAAG  CTGACCTTGG  CGACAGTGCG   10980
CGAAGTGGAG  ATGGCAGGTC  GCCGACAGAT  CATCGGCGCT  GTCAAGAACG  ACCCAGCTCC   11040
TAAGATCGTG  AAGGGCTGGG  CGAGGGTCGC  CACCGGGCGC  GAAACATGCG  CCTGGTGTCT   11100
GATGCTGATT  TCCCGTGGCC  CCGAGTACCT  TTCGGCGGAT  AGCGGGGGTC  TTCACCTCGA   11160
CACCGAGACC  GTGGTCGACC  TCTGGAACGA  GGCTGGCCGC  GATCTGGAGA  AGTTCCGCGA   11220
AGAGACCAAG  CCCCACATCG  AGGAGTGGCA  CGCAGGGTGC  GACTGCCTGG  TGGTGCCTGT   11280
CTTCGACGTG  GAGAACTGGC  CCGGAAAGGC  CGCACAGGAA  CGCGCTCTGC  AGCTCTGGAT   11340
CGACGCTGGG  AAAGAAGCCA  GCCAGCTCAT  TGCATCTGGC  AAGGCCCGCT  CCAAAAACGA   11400
GAACAAGGAG  ACGATCAACG  CTCTCCGTCG  CCGCTTGTAT  CGCGGCGAGT  TCGCAATGTC   11460
CGACTACGCA  CTCGCTGCGT  AATCCCCCGA  ACCCCAGGTG  GGTTCATCAA  CCATGCCCAG   11520
GAGGCGAAAA  CACATGTCCG  ACACCGCAAC  TACCGAAGGC  ACTCCGGCCG  GCGACCCGAC   11580
CCCGGTGGTC  ACTGACAAGC  CGCTGGAACC  GACTCCGAAG  ACCTACGACG  AGGCATACGT   11640
CAAGGAGCTT  CGCCAGGAGG  CCGCTGCTGC  TCGGGTTGCC  AAGAAAGACG  CAGTCGAAGC   11700
CGCAGTCAAG  GCGGCGAACG  ACGCTCACAC  CGCTGAACTC  GCTGCTCGCG  ACACTCGAAT   11760
CACCGAGCTG  GAGAACGAGC  TGGGACAGGC  TTGGATCCGG  CTGCAGAAGC  TGGAGACCTC   11820
GCTTGCCGCA  AAGGTTCCCA  GCGACAAAGT  GCTCGCGTTC  GTTGACATCT  TGCAGGGCGA   11880
GGACGCCGAC  TCGATCGCCG  AGTCCGCGAA  GAAGAACCTC  GAACTGATCG  GCGGTTTCGA   11940
CAAGAAGCCG  GTTTCCGGTT  TCGACCCCAC  CCAGGGCTTC  GGTGGTCGGC  AGGAACTGCC   12000
GCTCAACGGT  GACCCGATCC  TCAACGCCAT  GAAGGGCGTT  CTCGGCATCA  AGTGATGTCG   12060
AGCTGAAACC  CATTCCTAGA  CAAGGAGATT  AGCAGATGGC  CGCAGGCACT  GCTTTCGCAG   12120
TTGATCACGC  TCAGATCGCC  CAGACCGGCG  ATACCATGTT  CAAGGGCTAC  CTGGAGCCCG   12180
AGCAGGCGAA  GGACTACTTC  GCCGAGGCCG  AGAAGACCTC  GATCGTCCAG  CAGTTCGCCC   12240
AGAAGGTGCC  GATGGGTACC  ACGGGCCAGA  AGATCCCGCA  CTGGGTCGGC  GACGTGAGTG   12300
CCCAGTGGAT  CGGTGAGGGT  GACATGAAGC  CCATCACCAA  GGGCAACATG  ACTTCGCAGA   12360
CCATCGCGCC  CCACAAGATC  GCGACGATCT  TCGTGGCGTC  TGCGGAGACC  GTCCGTGCCA   12420
ACCCCGCCAA  CTACCTGGGA  ACCATGCGTA  CCAAGGTGGC  GACCGCCTTC  GCGATGGCGT   12480
TCGACGGCGC  GGCGATGCAC  GGCACCGACA  GCCCGTTCCC  GACCTACATC  GGTCAGACCA   12540
CCAAGGCCAT  CTCGATTGCT  GACACCACCG  GTGCCACGAC  CGTGTACGAC  CAGGTGGCCG   12600
TGAACGGCCT  GAGCCTGCTG  GTGAACGACG  GCAAGAAGTG  GACCCACACC  CTTCTGGACG   12660
ACATCACCGA  GCCGATCCTG  AACGGCGCGA  AGGACCAGAA  CGGTCGCCCG  CTGTTCATCG   12720
AGTCGACCTA  CGGTGAGGCC  GCGAGCCCGT  TCCGTTCGGG  CCGGATCGTC  GCCCGTCCGA   12780
CCATCCTCAG  CGACCACGTC  GTGGAGGGCA  CCACGGTCGG  CTTCATGGGT  GACTTCTCCC   12840
AGCTCATCTG  GGGCCAGATC  GGCGGTCTGT  CCTTCGACGT  GACGGATCAG  GCGACCCTGA   12900
ACCTGGGCAC  CGTCGAGAGC  CCGAACTTCG  TCTCGCTGTG  GCAGCACAAC  CTCGTCGCAG   12960
TCCGTGTCGA  GGCTGAGTAC  GCGTTCCACT  GCAACGACGC  CGAGGCGTTC  GTCGCTCTGA   13020
CCAACGTGGT  CAGCGGCGGC  GGCGAGGGCT  GAGCCTAACT  TGACATCCAC  CGGGAGGGGG   13080
CCGTTCACGC  GGCCCCTTCC  TGGGGTGTCT  GAGAGGACTT  CATGCGGATC  CAATCCACCG   13140
TCAACGGTGG  GTTCGCGGAG  GTCTCCGACG  AGTACGCCCA  GCGCCTGATC  GCGGCTGGCG   13200
```

```
GTTGGAAGCG TCCTCGGAAG CCTCGCACCA CCAAACCCAA ACCCGCTCCG AAGCAGGAGC   13260
CTGCGACCGA GGAGTAACAC ATGGCCTACG CGACCGCTGA CGACGTTGTG ACGTTGTGGG   13320
CCAAGGAGCC TGAGCCAGAA GTCATGGCGC TGATCGAGCG CCGACTCGAA CAGGTCGAGC   13380
GCATGATCCG GCGTCGGATC CCAGATCTGG ACGCCAGGGT GTCTTCGGAC ATCTTCCGGG   13440
CCGATCTGAT CGACATCGAG GCCGACGCGG TGCTGCGTCT GGTGCGTAAC CCGGAGGGCT   13500
ACCTCTCGGA GACCGACGGG GCGTACACCT ACCAGCTCCA GGCTGATCTG TCTCAGGGCA   13560
AGCTCGTCAT CCTTGACGAA GAGTGGACGA CCTTGGGAGT CAACCGACTC TCGCGCATGT   13620
CCACCCTCGT CCCGAACATC GTGATGCCGA CATGAGCGCC AGCGACGTTC AGCGGGCTCC   13680
GATCAAGTAC CCGCCGGGGT TTCTCCTGGC GGTCACACCT GACCAAGTCG ACGCCGCGAT   13740
GTGCGACCAC GAAGCGGATC CTCCGGTCTG CTACTGCGTC CACGACTGGC GCATCGAGTT   13800
CGGCAACGTC TCTCGCCAGC CCAAGCCGAA AGCGACGTAC ATCTGATGAG CCTCCTCGAT   13860
ACCGGAGCCC GGTACCAGCC GGTGCTCGTC TACCCCGAAG AGCTGGTCAT CGACGCGGAC   13920
GGGAACAAGA AGACCCAGCC GTCGAAGACC CCGATCCAAG CGATCGCACG CTTCCAGGTC   13980
GCCAACCAGT CCGGTACGTC GGCACGACGT GCTGAGCAGG ACAACGGGGG GTTCACGACC   14040
GAGAAGGTCT ACCGGATGCG GTTCCCTCGC TCCTTCACCA AGGAGCACGG GATCCTCGGC   14100
GCTCAGACCC AGATCGAGTG GAAGGGCCAG CGGTGGGCGC TCTTTGGAGA CGCCACCGAG   14160
TACGACTCAT CGCCCGCACT GGCGCGGGTC GACTACACGA TCAAGAGGTT CTGATGGCGA   14220
AGGTCTACGC GAACGCGAAC AAGGTCGCGG CCAGGCACGT CGATGTCCGC AAGCGGGTCA   14280
AGGAGGAGCG AGACGGCGTC ACCCGCCGTG CTCGAACCAA CCTGGCCAGA GCGAACAAGA   14340
CGACCCGTAT CACCAAAGAG GGGTACTTCC CGGCATCGAT CGAAGAGGTC GACGGCGATG   14400
TGGACTTCCA CACGGTCCTG CACGCGCCCA ACGCGTTCGC CCTTGAGTTC GGCCACGCCC   14460
CGTCCGGGTT CTTCGCGGGC ACCGACACGA AACCGCCTGA CCCCGAATAC ATCCTGACCC   14520
GAGCCGCCAT CGGCGGCACC GTCTCGTAAG GAGGACACAT GGGGGCGATG CCCCGAGTAC   14580
AAAGTGTGGT TGCTCCGATC CTCCGAGAAG ACCCTCGACT CGCCGGGGTC ACGATTGTGA   14640
CCTGGGTTCC CGACATCGAC TTCCGTGAGT TCCCGATGAT CAACATCCGC CGCATCGGCG   14700
GGATCAGGAA CGCCAACGCC CCGAAGCTGC ACTCGCTGCC GGTGGTCGAG ATGTCGGCGT   14760
ACTCCACTGA CGGGCTCATC GAATGCGAGG AGCTGTACGA GACAGCACTT GAGGTGCTGT   14820
ACGACGCGGT GAAGAACGGA ACACAAACTC CCGCAGGGTA TTTGAGTTCG ATCTTCGAAA   14880
CGATGGGCGC CACCCAGTTC AGCTCCCTCT ACCAGGACTC CTGGCGAATC CAGGGCCTGA   14940
TCAGGCTCGG CGTCCGCACA CCGAGATCCA CCACCTAACC GAAAGGTAGC CACATGGCAG   15000
AAAACGACGA TGCAGTTTTG ACTGCTGCGG TCGGGTATGT GTACGTCGCC GAAGCAGGCA   15060
CCGCTGCACA TACGCCGGCC GAACTGAAGA CCATCGACCT GTCCGACCCG TCGACCTGGA   15120
CTGGAGCCAC CGGCTGGTCG AGCGTCGGCC ACACCAGCCG AGGCACGCTC CCCGAGTTCG   15180
GCTTCGAGGG CGGCGATTCC GAGGTCAAGG CTCCTGGCA GAAGAAGAAG CTCCGCGAGA   15240
TCACCACCGA GGATCCGATC GACTACGTCG TGGTCCTGCT GCACCAGTTC GATGAGCAGT   15300
CGCTCGGCCT GTACTACGGC CCGAACGCCT CCACGACCCC CGGTGTGTTC GGTGTGAAGA   15360
CCGGCCAGAC CAACGAGAAG GCGGTCCTGG TCGTGATCGA AGACGGCGAC ATGCGCCTTG   15420
GCCACCACGC CCACAAGGCC GGTGTCCGTC GCGACGACGC GATCGAGCTG CCGATCGATG   15480
ACCTTGCCGC ACTGCCGGTT CGCTTCACCT ACCTCGACCA CAAAGACGAG CTTCCGTTCT   15540
CGTGGATCAA CGAGGATCTG TTCGGCCTCT CGCCGGGCGG TGGAGCCTGA CCCAAACTTG   15600
```

| | | | | | | |
|---|---|---|---|---|---|---|
| ACAGCCACCA | GGCTGTCTAC | CCCGGAGGGG | GAGGTTTCCT | TGGCGGGCCT | TGCCTCCCCC | 15660 |
| TCCTCCCGCC | ATCTAGCCCG | CCACACACTC | TGAAAGGTTC | GCCATGACAA | ACGTATTCAC | 15720 |
| GATCGACGCA | TTCCGCGAAG | AAGTCAAGAA | GAAGTACGAG | CCCGTCACGA | TCGGGATCTC | 15780 |
| CGAAGATGTG | ACCGTCGAGC | TGAAGCCGCT | GCTGAAGCTG | GGCCAGAAGG | CCCGCGAAGC | 15840 |
| CGTGGTCGAG | GCCGTCAAGG | AGGTCGAGGA | CATCCCCGAC | ATTGACGAGG | ACGACGAGGA | 15900 |
| GGCCGAGGAG | CTGGTGGACG | AGTACTCGCT | CCGCATTTGC | GAGATCGTCG | CCAAGGTCTT | 15960 |
| CCGGCTGATC | GCCACGAAGC | CCAAGAAGCT | GATCGCCGCG | CTGGACGAGG | AAGAGGATCC | 16020 |
| CAGGATCCGG | GCCGAGCTGT | ACGCGACCGT | ACTGCGGACC | TGGATGGTGG | AGACGCAACT | 16080 |
| GGGGGAAGCC | GCGCCCTCGC | CGAGCTGATC | GACAAGTTCG | GCGGGGCGAT | TCTCTCCGAC | 16140 |
| TTGTCCGAGT | ACCACGGGGT | CGACCTGCGC | GATCTGTTCA | GAGATGAAGA | TCCGCTGTCC | 16200 |
| CCCAGGTACG | TCCTGAATCT | GGTGATTCAC | CTCCCGAAGA | CAGGCGCGTT | CTACGCGGAG | 16260 |
| CGTCGAGGTG | GTCAGCAGTA | CCGAGGTTGG | GATGAGGACC | GGTACGCGCT | CGCGGACATC | 16320 |
| TACGACGCAG | TCCAGGCGGG | CAACCACATC | CTCCTGATGG | CCAACCGGGA | TCCGAAGAAG | 16380 |
| CCAAAGCCGA | AGGCACCCAA | GGCATACCCG | CGTCCCGACG | ACTTTGAGAA | GACAACGCCG | 16440 |
| AAGCCAGGTT | CGTTCGCCGC | GATGGTAGTG | GCCGCGAAGA | AGGCTGCGCG | AGAGAAGAGG | 16500 |
| GAAAGGGAGG | AGGCGAATGC | CGAATAGTGC | TGGCGTAGAG | GTCGCACGGA | TCTCCGTCAA | 16560 |
| GGTCAGCCCC | AACACCAAAG | AGTTCCGTCG | TGAGCTGAAG | ACCGATCTGG | AGAAGATCGA | 16620 |
| GCGGGAGCTG | TCGGCCGACG | TTCCGGTCAA | CGCCGACCTG | AACGCGGCCC | AGGCCAAGGC | 16680 |
| CGACTTCAAG | CGGCTGATGA | TGCAGCTCAA | GACCGAGGCT | GCCCGAGGTG | TCAACATCCC | 16740 |
| CGTCGATGTC | AACGTCGACA | AGGACACCAA | GGGCGGCTTC | CTGAGCCGCC | TGCTCGGCGG | 16800 |
| TAAGAAGGGA | CTGAGCAGTC | TTGGTGATGA | CGCCGCGAAG | GCGTCGTCTC | AGGTTCAGCA | 16860 |
| CCTGGGCAAG | TCGTTCCTGG | ATCTGACCCG | CACAGCGTGG | ATCGGCGTCG | GGATCGTCGC | 16920 |
| CATCGCCGCG | CCGCTTGTCG | GCTTGGTGGC | TGGCCTACTG | GCTGGCCTGC | CGTCGCTGCT | 16980 |
| GTCAGCGTTC | GGCGCTGGAG | CCGGTGTGGT | CGCACTCGGC | ATGGACGGCA | TCAAGGCGGC | 17040 |
| AGCCGAGACC | ATGATGCCCG | CGCTGGAAGC | GGCCAAGACC | GCCGTCTCCT | CGACGTTCCA | 17100 |
| GACTGGCCTC | ACCCGGTCT | TCCAGCAGCT | CGGTGGGTTG | CTGACGACCC | TCACCCCGAA | 17160 |
| CTTGCAGAAC | GTCGCCACCG | GCATAGTGAA | CATCGCCAAG | GGCTTCACCG | ACGTGGTGTC | 17220 |
| GCAGGGTCCG | GGGCTCCAGC | AGCTCCAGAA | CATCCTCGAC | CGCACTGGCG | AGTTCTTCAC | 17280 |
| CGGGCTCGGG | CCGGTCATCT | CGACCGGCAC | GCAGGCGTTC | CTGACGTTGT | CCAACGCAGG | 17340 |
| AGCCAACGCG | TTCGGACATC | TCCTCGCTCC | TCTGCAGGAG | TTCGCCAACG | GTTTCAACGA | 17400 |
| CATGGTCAAC | CGCGTCACGT | CCAACGGCGT | GTTCGACGGT | GCCATGCAAG | GGCTTTCGCA | 17460 |
| GACCCTAGGC | AGCATCCTGA | ACCTGTTCAA | CCGGCTCATG | GAGTCCGGTC | TGCAGGCGAT | 17520 |
| GGGTCAGCTC | GGTGGTCCGC | TGTCGACGCT | CGTCAACGGG | ATCGGTGATC | TGTTCATCGC | 17580 |
| GCTGATGCCC | GCGCTGACTT | CGGTGTCGAG | CTTGCTCGGC | AACGTCCTCG | GGACTCTGGG | 17640 |
| CACTCAGCTC | GCTCCGATCA | TCACGGCGCT | GACGCCAGCG | TTCACCACGC | TGGCCGACAC | 17700 |
| CCTCGGCACG | ATGCTGACGG | GCGCTCTGCA | GGCTCTGGGG | CCTGTGCTGA | CCGTGGTCGC | 17760 |
| TGAGACCCTC | GGCACTGCGC | TTACCACTGC | GCTGCAGGCG | ATTCAGCCGA | TGCTGCCCAC | 17820 |
| GCTGGTGGAC | AGCTTCAAGC | AGCTCTCCGA | AACGCTGGTC | ACCTCGCTCG | GCCCGTACCT | 17880 |
| GCCCCAGATC | GGGGAAGCGT | TCGGCCAGAT | CGTAGGTGCG | GTCATTCAGT | GGCCCCGAC | 17940 |
| GATCATCTCG | TCGCTGATCC | CAGCGTTCCA | GACGCTGATC | CCCGCGATCG | CACAGCTCGC | 18000 |

```
TCCGTCGCTG GTTCAGATCG TCCAGGCGTT CACCAAGCTG ATGCCGGTCA TCGTGCCGGT    18060
GGTCCAGATC GTCATCAACC TGGCTGCGGC CGTGGTGCAG GCTGGCGCGT CCATCGCGTC    18120
GTTCCTGATC GGTGGCATCT CCCGGCTGGT TGGCGTCCTG GCAGACTGCG TCGGCGCAGT    18180
CGCCGAGTGG GTCGGCTCCT GGTCCAGCGG TGTGCAGCAG GTCTCCGACT TCGTCGGACA    18240
GCTCCCCGGC AAGATCAAGA GCTGGTTCGA TGACGCAGGC TCCTGGCTGA TCAGGCGGG    18300
CAAGAACGTC GTCCAGGGTC TGATCAACGG CATCGGTTCG ATGATCAGCT CTGCGGTGAG    18360
CAAGGCCAAG GAACTGGCCA GCAGCGTGAA GAACGCTGTG ACCGGCTTCC TCGGGATCCA    18420
CTCTCCGTCA AGGGTGTTCG CTGAGATCGG TCAGTTCACG GCCGAGGGCT TCGGCAACGG    18480
CTTCGAGGAA GGGTTCCAGC CCGTCATCGA GAAGGCCAAG GCCCTGGCGG CTGAGCTGTC    18540
TCAGGCGATG GAGTCTGGCG TGGACCCCTC CGGGATCCTC GCTGGTATCA GCACCAAGGA    18600
ATTGAAGCAG TACTCGGCTG CGCTGGAGCA GGAGCGCAAG CGGATCCAGG TCGAGAAGAA    18660
CGCAATTCCC AAGGAGGACA AGGCCGGCCG TGCGGCGCTG CAGGCGCAGC TCGACCAGAT    18720
CAAGGCGCAG AAGGACATCC TCGCGTACCA GAGGGACCGC ATCAAGAACG AGGAGGACTA    18780
CGTCGGCGCA GCGGGCGATG ACCCGCTCGT GAAGGCGGCT TCCGGCTTGA TGAACGCACC    18840
GGTCGACTTC GCGAAAGCGA CTGGGAAGCA GTTCCTTACG GACCTGGGTA TCTCCGGGGA    18900
CGGTGCGATC TCCAAGGCCA TCACCGAGGG GATTCAGTAC ATCTTCCAGA TCGGCTCTGT    18960
CGATGAGGCG CTGTCGATCA AGGACCGCGA GGAATCCAAG AACGCGCTGT CGGTCGTGGG    19020
CCGAGCTTGA CATCCACCAG GAGGTAACCA TTGATCACCG ACACCATCGT TGAACTCGAA    19080
GGTGTCAACG GTGAGCGCTT CAACTTGACG ACCGGTGACC AGGGCGTGTT CCTGGCCACA    19140
GACGTGGAGG GTTGTTTCTA CGACCCTCCC GTCAAGGTCG TCTACGAAGA GCCGGGGAAC    19200
TACCCCGGTG CTCGCTACCT GGGACACCGA GTTCTGAAGC GCGACATCGT CTTCGGGGTT    19260
CAGATCCTCA ACGACGCGAA GCAGGGACCA CGGTCCTGGC TGTCGCGAGA CTCCGTGTGG    19320
CGTAAGGCAT GGGCGTTCAA CCGCGTCTGC AAGCTCTACG TCACCACCCC GGACTCCGGT    19380
ACCCGGTACC TGTACCTGGC GCTGTTCGAG TCCCCCAAGG TCGAGATGAA GACCGACCCG    19440
CGTGGCAACA CCATCAACCT GACGGTGATG TCGTGCATCT CGTACGACCC GTTCTGGTAC    19500
GAGGACGACC GAGTGTTCTC GGTCAAGACC AAGACCGATA CCAGGTTCGA CCCGAACTTC    19560
TGGACACCGC CGTGGCCGTG GGAGGAACTG CCCAAGGAGA CGCTGCGGAT CAAGGTCGGC    19620
CGCGAGCAGG GCGGGCTCAA CCCCACCGAC CAGTACATCG CACCGAAGTG GACCGTTCCC    19680
GGCTCCACCG AGAAGATCCC TGACTTCCCC TGGCCGTTCC CGCCGGGAGT CGAGATCCCG    19740
TGGGAGACCG CTCCGTTCAC GCAGTTCGTC ATCCCGGACT ACTCGTTCGA GGACGAGGAG    19800
TTCGCCAACC GCCGGCTCAA GACGCCGGGG TTGATCTACG GCGAGAACTG CATCATCGAC    19860
ACCGACCGAC GCGAGGAGCA GATCAGCTCC GAGTCGGGCT CCCCGGTGTG GGCGCGGATG    19920
AACGGTGTCC GGTTCCGCAA CATGATCCCC CCGTACACAG AGGAGCGTGA GTTCGTCATA    19980
GACGCATCGG GATGCGCTCC GGGACAAGTG GTTACCCTTC GGCTCCCGAG GCCGTGGTCG    20040
CGCTGCTGGG GTCTCGAATG AGTGGCCTGA CGAGCGTTGC CCAGGCTGAA GATCTCTGGC    20100
GGAAGATCCA ACTGCGGCGC TGCAAGCGCG AGCAGGAGCG ACTGAAGCCA CCGGACGTAG    20160
AGCTGCGCGA CGGCGACTTC CGTCTGCGCG GCCTCGTCGC GGGTGAGCGA CTGCTGGAGT    20220
GGGAGTTCAT CGAGAACGAG ACCGGCGTAG CCACGCTGCA GCTCTCGCTG AGCCACTACC    20280
TGGCCAAGTG GGTGATGAAC CACCGGGGTC GAGCAAAGCG CAACGTCATC CTCAACGTCG    20340
AGAAGCAAGG CGCTCGATGG AGCGGGATGA TGGACCACTA CCGGGTGGTC AAGGAGGACT    20400
```

| | | | | | |
|---|---|---|---|---|---|
| CCGGGGACTG | CTACCTGGAG | ATCGTGTTTT | TGCACGACTT | CGAGCAGACC | AAGCACATCC | 20460 |
| GTGTCTGGTG | CAACCCGTTC | CTGCGCCCTG | AGCTGCAGTT | CCCCAAGATC | TGGATCATCT | 20520 |
| TCGGGCCGGC | CAAGTGGTGC | TTGCTGGTCA | CGCTGTTCGT | GAACCTGCTG | CGACTGGAAA | 20580 |
| CGTCCCTGTG | GACGATCCCC | GACGATCCGA | CGGACATCTG | GGAGTGGATG | GGGCCGAGCT | 20640 |
| TCAACCCCAG | CAAATGGCGG | AACATTGTCA | AGCCGTTCCC | CTTCCTGCTG | ACAACTCGC | 20700 |
| CCATCACGAT | GGTGTTCAGC | CGGTTCGGGA | CGTTCTACGA | CACGGCGAAG | CAGATCCTTG | 20760 |
| AGAACCACCA | GCTCACGCTG | ACGTGTCGCC | GGTACATCAA | GGACCGCGAC | CCGCACCCGT | 20820 |
| TCGATGACCT | GAAGGGTCTG | TGGGGCATCG | ACCCCGTCGA | AGGTCTGTTG | CAGCTCATCC | 20880 |
| CACTTCGGGA | TGGCTGCGTG | GTCTGGGACA | TCGAGGACAA | CTCTGGCTGG | GGCACCGAGA | 20940 |
| CCGCCTTCGG | CGGCTCCTGG | CTCACCGGGT | TCGTCCGGGC | GGTCGTCAAC | CTGGCTGGAG | 21000 |
| ACGGCCAGGT | CGAAGGGGTC | GACGTATTCA | CGGGTGACTA | CACGTTCCCC | GGCGAGTACT | 21060 |
| ACTCCCCGTG | GTTCCTGGGC | ACCAGCCCGA | GGGCTCCGCA | CGTCGTGTTC | GAAGAGGGGC | 21120 |
| CACTGACCGG | GATCAAGTCG | TCGGAGTTCT | CGTACTACGA | GGCAACCGAC | ACCAGCTTCC | 21180 |
| TGGCCGGTGG | ACAGTCCGCT | CCGGGCATCA | ACGAGGGGAT | CTCGGCCCTG | GTGAACATCG | 21240 |
| GTGGCGATCT | GCTGACCTCG | TTCATCAACA | GCCAGCTCGC | CGTGCTCGGC | GCGGTCGGTG | 21300 |
| GCGCGATCGA | CCTGCCCCCG | CTGGGCGGTC | TGATGGATGC | GGTCCTGAAC | CCGCTCTACT | 21360 |
| CCGACGTGTT | CGGCGCGTTC | ATGGAAGTCC | CGACGCTGCG | TGCGATGGGT | ATCTCGCTTC | 21420 |
| CCATTGCGGG | GCTTGAGGAC | ATCGTCACCG | GCCTGGGCGA | CTTCCACTAC | TACGAGAACA | 21480 |
| TGGTGGACAG | CCCGATGAAG | GCGTTCACCC | TCTCGGCGTT | CGCGGCCATC | GCAGCCCAGA | 21540 |
| TCCACAAGAC | CCGAGCCCGA | ACGGCTCACA | CGCTCAAGGT | GTCTGACGCG | GCACCGTACA | 21600 |
| TCTTCGCACC | AAAGCCCTAC | GGGCACTGCT | GGATCGGAGA | TCGCGTCGGC | ACATCGGTGC | 21660 |
| TCGGCTACCC | GGTCGAGCAT | CAGTTGTTCG | TGGAGCGGAT | CCGAAAGGTC | AAGTACCGCA | 21720 |
| TCGACAAAGA | CGGCATGAAG | CCGTTGGAGA | TCGAGATCGG | ATACCGCGAA | CCGAAGAACC | 21780 |
| CAGCTCTGCA | CATCCTCGAA | GAGATCAAGC | GTTTCAACGG | CGCTATGGGA | CAAGCGGGGA | 21840 |
| TTCTCTAACC | GAAAGGCACG | CCGCATGATT | CCGTCACAAG | AGACTCACAA | TCCGAACGAC | 21900 |
| CCGCGACAGC | ACGTCGTCTG | GGCGCTCCGC | AATCTCCCGT | TGATTGCAGG | CGTCGGGGCG | 21960 |
| ATCACGCATC | CGGCGTACCT | GGCGGATTGG | TCAGAGCACT | TGTGGAAGTG | CGGCTTTCGG | 22020 |
| CATGTCGACT | GGCTCCGGGA | GCTGGCTGAT | GAGGACGGCA | ACATCCACGT | CAGTCAGCTT | 22080 |
| CCTGACCAGC | AGATCAAGTT | CCAGCCGGCC | TTCCGAGGCC | AGCGGCACGA | CATGAACAAC | 22140 |
| GCAGCGAGGT | GGGCCGAGAA | GGAACTGGCT | CCGGGAGCTG | GCTGATGAGG | ACGGCAACAT | 22200 |
| CCACGTCAGT | CAGCTTCCTG | ACCAGCAGAT | CAAGTTCCAG | CCGGCCTTCC | GAGGCCAGCG | 22260 |
| GCACGACATG | AACAACGCAG | CGAGGTGGGC | CGAGAAGGAC | GCTCCCGACC | CAGAACCCGT | 22320 |
| GCGTATCCCA | GACATTCGCA | AGCTCACAGA | CCAGGAGAAC | CGAGCGATGC | TCGCACAGTA | 22380 |
| CGAACGAGAC | GGGTGGATCA | AGAACGACCG | CCCCGGCCCA | GCGATGGCCG | AGGTCGTGGA | 22440 |
| GTGACGGAGC | TATTCAACCC | CGATAACCCT | TGGGAGACAG | CACTTTTGTT | CTTCGCCGTG | 22500 |
| TTCTGTTCGG | TACTGCCTGC | GTTGCTTCCG | TTCTGGTTCA | AGATCAAGAA | GATCGACAGC | 22560 |
| CAGGTATCGA | ACTCGCACGA | CGAGAACCTC | CGCGACGAGA | TCACCCGAGG | GTTCAAAGAG | 22620 |
| GTCCGCGAGG | ACATCCGACT | TCTACATGAG | GCGCTGAACA | TCGAGCGCCG | CGAACGCATC | 22680 |
| GCTGGTGACG | AAAAGAGGTG | CGCTTGACAT | TCCCAACCAA | CCCACTCGAA | GCGATCGGAG | 22740 |
| CTGACGGCGC | ATTCGAGATC | GGCGGCGGTG | ATTTCAGCTT | CGGCCAGGAC | TACACCGAGC | 22800 |

```
AGATCATTCG GTCGCTGTTC ACGATGCCGC CTGTCCGACT CGACAACGCG ATCACCCTCC 22860
TCCGCGAGCA CCTGCTGAAG CTGCCTCTGG AGGCGCTGCA GAGGTTCAAG GAGATGATCC 22920
CGGACTGGGC CGAAGGCGCG TTCGACACCG CTACCGGTGC TGTCGATGCG ATCATGGACG 22980
CGCTCAGCGA AGGTCCGCTG TTCCTGAAGC TCGCAGAGTT CCAGGTGTTC CTCCAGCGGC 23040
TGCTGACCGA ACCCGGAGAG GTCATCGGGG AGATCCCCCA GGCTCTGGTC AACGGTCTGA 23100
CGAGCGCCCT GGAGACCGTG AACAACACGA TCCAGACCAT CGTGGACATG CTGCTGCAGG 23160
CCCTCGGCAT CAACCCCAAG GGCGACCTGC TTGACCGGAT CTTCGACCTC AGCGACGAGA 23220
TCGAGTGGCT GCGGGACACC GCGAGCCAGG TAGCCTCCGG GCTCCAGCAG ACGTGGAACC 23280
ACTTCTGGTC GGCCCTGACC GGGCGCAGCC CGGGCGAGGA CCAGACCGTC GTTGAGCCGG 23340
CCGAGCAGAT CGGTGAGCTG GCCGGTACGA CTCAGTCGAA CTCGTCTGCC ATCGCCGAGC 23400
TGCAGGCTCG CCTGGACGCA CAGGACCACA CCGGCATCGC TGGCGGGGAT GACTTCGAGC 23460
GAGTCAACAC CACGGCGGTC GGCCCCGGCT GGGCCGAGTT CTATACCGGC GGCGGCTACG 23520
GATCGGGCAG AGGCTACTAC GCGATCAAGG ACGGCCATCA GGCCGAGTGG ACCGACCAGG 23580
GAGCCACACA GAACACCGCA CGGTTCGTCC GTACGGACCC GGCCGACGAG AAGACGGTCA 23640
CCGACTACCA GAAGATGACG CTCGTCGTCG GCACCATCCC CGGTGAGGCT GCAGGCCTCT 23700
TCCGGGGCGG CTCACACATC CGGTTGTGGC TGCGCGTCAA CGACAACGCG CCTACGGTCG 23760
GCATCACCGA CGGGGTCTAT GTCGAGGTCG GTGGCGCGAA CCTCGCGCAG TTGGGCTACC 23820
GGCGTAGAGG CTCTGACCAC TTCGTCGGCT CGGCGTTCAA CTGCTCCTGG GGAGCCGGGA 23880
CCATCTTCAC GTTGGTCGCT GGCACGGTCG ACGGCATCGA GAAGGTCGAG TTCTACAAGA 23940
ACGGCTCTCG ACTGGCCCTG TGGTCCGACG ACGGGCTCCG GTCGGCTATC GGCGCTGGCT 24000
TCCGGCGCTG GGGCTGGGAA GGCCAGGCCC GTAACCGCAA CCTCGGCCAG GGCACCCCGA 24060
GTTCGGTCAC CCGCGTCACG ATCAACGACA ACGACCCCAG CGGTCTCGGT GGCGGCTCGG 24120
TCCACCTCGA AACCGGCGTC GTCGGCATCC TGCAGATCCC CAACGGCGGC ACAGGTGCTA 24180
CCAGCGCGGC CGAAGCCCGC GCCAACCTCG GTGCCGAGGC GGCTATCCCG CAGGGACCG 24240
TCGCGCAGTA CTGGCGCGGC GACAAGACGT GGCAGCCGCT GAATAAGGTC GCTGTAGGGC 24300
TCCACCTGGT CGACAACACG TCGGATGCCC AGAAGATGTC GGCTCCGCC GTGCTGACGA 24360
ACAAGACGAT CTCCGGGGCT GACAACACGC TCACCGACAT CCCAGTGGCA GCACTGGGTC 24420
TCGGAGCCGT GAACGCAGTG CGGGTAATCG CGGGCGTTCC GATACCGAAC TCTGTGACGA 24480
TCTGGATCGG GACTGAGGCC CAGTTCCAAG CTCTCCCAAC GAAAGACGCC AACACCCTGT 24540
ACTTCAGGAC GGCGTAATGG CGGGGATCTC GTCAGGGCTC GAAGGCATTC GGGCCATCTC 24600
GTGGAACACC GTCCCCATCC TGAAGGTCAG CCTCGGCAAC GACCAGGTGT GGCCAGCGTT 24660
CGACCCGGTG CTGACTCCGG TCACGGCGGT CGGCGCGTAC ACCTACAACA TCCCGGCACA 24720
GGCCGAGTTC ATCGACGTGA TTCTCCTCGG AGCTGGCGGT GGTGGACAAG GCATGGGCTC 24780
CGCCACTGCG TGGGGCCAAG GCGGCTTCGG CGGTTCCTGG GTGACGGCCA CGCTCAGGCG 24840
TGGCGTCGAC ATCCCGTGGG CGGTCACACA GATCACTGGC GTCATCGGCG CTGGTGGTAC 24900
CGCAGGGCCT GGTTACATCT TCGGACAGAC CGGCGCGGGC GGCAAAGGGG CGACACCAC 24960
AGCCACCTTC TCGGGCGGTG GCACGCTCAT CGCTGCCGGT GGTGCTGGAG CAATTCGAG 25020
GAAACTGGAC TTCGGAGGTA AGTCCCCGAA TCCTGCCGAC ATGGTGTACC GAGACCGGAC 25080
CTACGACGGC GGCGCTAGGC AGCTCACCCC AAGTGGTATC GGGTACGCAC CTGGTGGCGG 25140
CGGCGCAGCC GCAACGGTCC CAGTGGGTAT CACCGGTTTG GCCGGTGGTC CCGGTGCCCG 25200
```

| | | | | | |
|---|---|---|---|---|---|
| TGGCCAGGCG | TGGTTCCTGG | CGTACTAAGG | AGGACGATGG | AGTACGACTA | CGCCCTCCGG | 25260 |
| TACGAGGGCC | AACAGACACC | CGATGGTCCG | TGGGTGGAGG | TCATAGTTCC | CGCAGCCAGC | 25320 |
| CTCGCAGAGG | CTCGGGCCGG | GTACGAGGCG | AGCCTGCCGA | CGATGATCGA | CAACCCCAGC | 25380 |
| ATCCGCAATC | TGCAGATCGT | CTACACGCCC | AAGATCCAAT | GGACCGTGTG | GACTGAGTGA | 25440 |
| CAAGAAACCC | CCCTCTTGAG | GCTGTATGGC | CTTGGGAGGG | GGGCTTTTTG | CGTTTCAGGG | 25500 |
| GGTAATCCCT | GCCAGCTCCG | ACATTCGCCT | CGCTATCTCC | TCGTCACGGG | CTGCTGAGGC | 25560 |
| CATCTGGTAC | TTCATCGCCA | TGCGCGGAGT | CGTGTGCCCG | AGGCGCACCA | TCAGCTCCTT | 25620 |
| GGTCGTCGCA | CCGGCCTGAG | CCGCCAGCGT | GGCTCCCACG | GCCCGGAGGT | CGTGGATGCG | 25680 |
| GAGGTCCGGT | CGACCGATCT | TGGCGTAGCC | CTTCTTCAGC | GAGCGAGTGA | ACGCAGACTT | 25740 |
| CGACAGCCGC | TGCCCCCGCG | TGGTGGTCAC | CAGGAGAGCT | TCCGGCCCCT | TGTTCATCTT | 25800 |
| CGTCCGGTCA | GCCATGTGCT | CGCGGATCAT | CGCCGCGACG | TGAGGCGGCA | CGGTCACCGG | 25860 |
| CCGCTTGGAC | CTGACGGTCT | TGGTGTTGCC | GACGACGATC | TTCTCGCCGA | CGCGGGCCGC | 25920 |
| GCCCCGGCGC | ACGCGGAGCT | TCATCGTCTC | GCCGTCATCC | ACGATGTCCT | TGCGGCGGAT | 25980 |
| CTCGATCAGC | TCACCGAACC | GCAGGCTGGT | CCACGCCAGG | ATGTAGACGG | CCACGCGGTA | 26040 |
| GTGCTCGAAC | ACCTCCCCGG | CCACTACGTC | CAGCTCCTCC | GGTGTGAGGG | CTTCCACGTC | 26100 |
| GCGCTCAGCG | GGTGCCTTCT | GCTCGATCCG | GCACGGGTTC | TCCGACACCA | GCTTGTCCTC | 26160 |
| TACAGCGGTA | TTCATGACCG | CCCGGAGTAC | GTTGTAGGCG | TGCCGCCGTG | CCGTCGGGTA | 26220 |
| CTGCTTACCC | ATCCGGCCC | ACCACGCCCG | GACAAGGGCG | GGGGTCATCT | CGGCGACCGG | 26280 |
| GGTGTCGCCC | AACACCGGGT | AGATCCGCTT | GCGAGCGTGC | GTGCTGTAGA | GATCCTTGGT | 26340 |
| GCCGCCAGCG | AGGTCTCGCT | CGGCGATCCA | CTTCTTGGTG | TACTCCTCGA | CCGTGATGGC | 26400 |
| ACTCGCCGCA | GCCTTCTTCT | CGCGCTCGGC | CGGCGGGGTC | CACTCCTCGT | TGTCGATCAG | 26460 |
| CCGCTTCTCA | GACGCGAGCC | ACGCTTCGGC | GTCCATCCGG | TTGTCGTAGT | TCCTCGGCCC | 26520 |
| GAAGTACCGC | TGCCCGTCGA | TCGGGCTGAC | GTACGACGCT | TGCACTCGAC | CGCTGCGCTG | 26580 |
| GGTCCGCAGC | GATCCCCATC | CTCTCCGTCT | TGCTGCCATG | CGAAACAGGC | TACCGGAATG | 26640 |
| CGACCTTATT | GCGACCTTCA | GACGTCTTTG | CGTGTCCGTG | AACAGGCATT | TTTGTCCACT | 26700 |
| TCAAGGTCGC | ACAGGGTCAG | AGCTAAAAAC | AGGGTCTGAG | CTGGGAGAAT | GTGACACGCC | 26760 |
| GACCCCCTTA | CTTCCAAACT | AGCTACGCGG | GTTCGATTCC | CGTCGCCCGC | TCCACAGGTC | 26820 |
| AGAGGTGGTT | TTTAGCCCGA | GGACCGGATC | CCCGAGAGGG | GGCCGCGACC | TTAGAGCGAC | 26880 |
| ACTAATGACC | TGCATTTATG | CTGCCCGGAT | ACAGCGACAC | ATCTGCTACC | TTCGACCTCC | 26940 |
| GACAGACGAA | GAAAGCCCCC | CGCCTGCTGC | AACAGACGAG | GGGCGGTACA | CCAGATCGGA | 27000 |
| GCTGGTGCAG | TGAAGATTCT | CTCACGTGAC | AAGGTCGCAC | TTAAGGTCGC | AACGGCCGGA | 27060 |
| ACCGTCGCCG | TCGGCGGTCT | GGCCTTCAGC | CTCAGTTTCA | CCGCGCTGAG | CGAGCTGTCA | 27120 |
| GCGGCCAACG | GAGTGGCTCA | GTCGTGGATG | GTCCCGCTCG | TTATCGACGG | AGGCATCCTC | 27180 |
| GTCGCGACGA | TGGCGACCGT | GGCCCTGAGC | CGACACGGTT | GGTACGCCTG | GGCGCTGCTG | 27240 |
| ATCCTCTCGT | CGCTGATGTC | GGTCGCGGGC | AACGTGGCCC | ACGCCCAGCC | TCACGGGCTC | 27300 |
| ATCGCGATGG | TGATCGCGGC | GATTCCGCCG | TTGTGGCTCC | TCGCATCGAC | GCATCTGACG | 27360 |
| GTCCTCCTCT | ACCGGGAGGC | CCAGGAAAGT | GGCTCAGAAT | CGATCTCAGA | GCCTCTTCTG | 27420 |
| ACCAGGGGTT | TTGCCGAAGC | AGCTTGACTG | CGCCCGACCG | GGCATAAAGT | ACATAGACAG | 27480 |
| ACTATGTATT | TAGGAGGCAC | AAAAAAAGGG | CTCCAGAAGG | GCCAGCACGA | AGCCAGCCCC | 27540 |
| TCCAGAGCCC | AGAGGGTGCT | ACCGGGTAGC | TCACTTACCG | ATGGGCGCA | TCAGCGCCTC | 27600 |

```
GACGGAGTCA CGTTCGACGC GGATCAGCCT GGGGCCGAGC CGCACGGCCT TGAGCCGGCC    27660
GTCGGCGATG TAGCGGCGCA CCGTCTTGGT GCTCACGCCG AGGAAGTCGG CGGTCTGTTG    27720
GATGGATGCT CTCTGCGGCA TTCAGCTCTC CTTGGGGTAG ACGACGCGCT CGATCCCGGA    27780
TGCAGCGATC AGGTTCGAGC AGGCGTAGCA GGGCTCTCGG GTGACGTAGA GGGTCGCTCC    27840
GATGAGGTCT TCGCGGTCGC AGTAGAGCAG TGCGTTTGCC TCAGCGTGGA CAGCCACGCA    27900
TCGAGTTGCT CCGCTGCTGT AGTCACTGAC TCCAGGAACC GCCCCAGAGA GTCGGCGAGG    27960
GCACGTACTG CATCCTGCAG CTCCCGCAGG CGCTCCGTTG TAGCCAGTTC CGCGAACTCG    28020
TCGGTCCTTG ACGACGACTG CACCAACCTT GCTCCTTTCA CAGTCCGATC GCTGGGCCGC    28080
TGCCGTGGCG ATCCCGAGGA AGTACTCGTC CCAGTCCGGT CGACTCATCA GAAGAAGATC    28140
GGCACGTTGA CGCCGCCCCC GGCGGGCACG AAGATCACGC CGTTCGGGCC GGTGTAACCG    28200
GGTGCGGAGC CGCCACCGTC ACAGGCCGTG AGGCCCAGGG CGAAAGCGAC GACGAGCAGC    28260
AGGACTGCGA TGGTCTTCAT GAGGTCTCCT TGTCGAGTTG TCGTTCCAGT TCGAGGATTT    28320
GGGCCTTGAG CCCTTGGTTC TCCAGCAGCG CCTCGGCGAG CTGGCCTTGT GCGATGTCGT    28380
TGGCCTCGTC CTTGCGGACG GCCTCGTCGG TAGCGTCGTG CAGTCGACGG ATCAGGTCCG    28440
GGAGGGCTCC GTGGAGACCC GCGACGAAGT CCGCGTCCTG CTCCCGGTGG AATGAGCCGA    28500
GCCACAGCTT GCTGCCGTCG GTCTGGTCGA CAGCGAAGAC CTGCCACTGC AGGTGCTCGT    28560
CACCGTCGAA CTCGACCACC CAGTAGCGGG ATTTGGCCTC CGTGGTGTGC GACCACTGCT    28620
GGTACAGCAC GTCGAAGAAC TCGTGGTCCT CAGCCTCGTA CATCGAACTC CTTCATGATT    28680
CGGTCGAACG CTCGCTGCTG CACGCGCATC TCCAGGGCAA CCGTCCGCTT CAGCCACGCC    28740
CACTCGCCGT CGTGGTTGAT CTCCCACTGG CTCTTGAACG CCACATCCTC GACAAGGAAA    28800
TCGACTGTCA GCGTGTGGAT TCCGGTGTTG CTCACCTGGA AGGTGATGCC CTCCTCGGCG    28860
ATGTACCAGG GCAGCTCCTG GCCGTCGAAG AAGACGGCCC GGTCTGTCAC CACGACATCA    28920
GGAAAATGGT GCATCGTTGA TGTACCCCTC CTTGGTGAGG GCCTCGAACA CCTGGTCCAC    28980
GACCTGGTTG ACGTGGCCCC CGAACCAGAC CGGAGCCATG TGCTCGAACG CAGAGAACGA    29040
CTTGTGGGTC AGCACCTTGC CGTCGGGAGT CCGAACACGA AACTCGAACT CCCAGTTGAC    29100
CTTTACGTCG TCGGCCATCA GCGCCGACCC AGGTACGGGA TGATGTTGGC CCGGAACTCG    29160
AAGTAGAAGC CGGGAGGCCG ACCTTCGGGG ACATCGGCGG TGTAGACGCC GATCTCGTCT    29220
CCCTCGATCG TGCCTAGCTG GCTGAGCTTG TGGATCGCCA GACCATCAG CTCCTCGGTG    29280
AGCTTCCCGT TCGGTGCGGG CAGCACTACG TTGGCTTGTG CCATCAGTTC TTCTCCTTCA    29340
GTAGTTCTGC GATTGCGATG AGCGCGTTCA ACTGCGCCAC CTTCAGCTCG AAGTCCGCGT    29400
CGAAGGTCAT CCGACGGCGA CGAGCCACCC TCTTGGCTTC TTCCAGGTAG TTGGTGTCTG    29460
TCAAGTTGCC CTCCTCAGTA ATCAGCGCCG TAGAGCGAGC CCACGAACG CTTTCCAACT    29520
TCGGGGTCGG TGCCGATCAG CACCGGACCC ATCTCCTCGG CCATCAGTCG AGCGATCTCG    29580
CGAGCGCCCC AGTTGGCCTT CTCAGCGGGC AGAGACGCGA CGATCTCGTC GTGGATGGGC    29640
AGACGTAGGT ACGGGGTGAA TCCGGCTTCG TGGAGGCGAA TCAGCGCCTT GCAGGTCACA    29700
TCCCGAGACG TGGACTGGAT CTGGTAGTTC AGCGCCGAGT ACGTCCGAGA GCGGTCCACC    29760
GGCAGCCGCC GGCCCATCGG GTTGATGATG TACCCGTTGC GCTTCGCCTC GTTGGCGAGC    29820
TTGCGGCTGT ACCGCGTCAC TCCGGGATAC GCCTTGTCGA ACCCGTCCAC GACCTGCTTC    29880
GCGGTCTCGA TCGAGATCCC AGTCTGCTCG GCCACCGTGT TGGCCCCACC GCCGTAGACC    29940
CGGCCGAAGT TCACCGTCTT GGCATACTTC CGCTCCGGGT CGTCCTTGGT GATGTGGTCC    30000
```

```
CCGAAGGCAG CGCGAGCTGT CATCAGGTGG AGGTCCGCAC CGTCCTTGAA CGCCTGGATC    30060
ATCGTCCGGT CGCCCGAGAG CGCGGCCAGG ACGCGAAGCT CCTGCGCCTG GTAGTCGATC    30120
GAGGCCATGA CGTGACCGGG GTCAGCGAGG AAGCACCGAC GCACCGTCCA GTCGGACGCG    30180
GGCAGCGTCT GCGCCGGGAT GCCAGTGATC GACATGCGCG AGGTCCGCGC CTGCAGCGGG    30240
TTGACGAACG TGTGGCACCG GTCCTCGGAG TCCGAGTGT  CCAGGAACGT CTGGACCCAC    30300
GACGTGCGCC ACTTCCCGAG CTTCTTGGCC TCCTGGACCA TCTCGGCCAG GTGAGCTTTC    30360
TCGCCTCCCG CAGCGATCAT GTCCGCGTAG AACCCCTTGT CCACCTTCCG CTTACCGGAG    30420
TCGGTGAACG CGGTGAACTT GTGTCCCAGC TCCTCGAACG CCTCCGCGAC ATCCTCGGTC    30480
GCGTTGACCT TCTCGATCCC GTACTCGTTG AGGAGCACGG CCTCCCAGAC CTGCTGCTCC    30540
CCCAGCCACT TGTCGGCAAG CTGCTGCGAG TACTCCACGT CGAGCAGGAA CCCGCGCCGG    30600
TCGATGTAGC TGCAGATCTC GGAGATCTTG TGCTCGTACG GCACCAACGG CCGGCTCACG    30660
TCGGGCACCA GCGGTGCCAG CGCACTGCAG ATCCGGGCCG TGAAGACCGT GTCCATCCCC    30720
GCGTACGTCA GGTACTCCGG GTGGTACAGG TCGATGGTCG ACCAGATCTT GGCCTTGGTC    30780
GTCTTGTGCT CCTTGGCCAG CTTGGCCATG AGCCCCTTGA CGTTCTCAGC CTGCTCCTTC    30840
GAGATGAACT CCGCGATCAG CTCCTCCAGC GAGTGGCCGA ACCCACCGGC CCGAAAGGC    30900
CGGGGGTCCA CCAGCTTCGC CAGGATCTGC GTGTCCAGGA TCTTAGGCCA GAGCGACTCC    30960
ATCTTGATCC CGAAGCACCG GTCGAGCACC TGGAGGTCGT ACGAGGCGTT CTGCATCACG    31020
ATCTTGTTCA GCACGTCGAG CGCCTCATGC ACCTCCTCCC GCCCAGCAT  CTCCAGATCC    31080
TCGATGGGCA GCACCCAGGA TTCGGTCTGA GTACCGAACT GGACTAGGCG GCAACGGAAG    31140
TCGGCGCTGT AGATGTCCAG CCCGGTGGTT TCGGTGTCGA CGGCGAGGCA GTTCTGATGA    31200
GCCCGGATGA AGTCGCGGAA GCCGTCCAGA TCCTCTGGGT GTTCAACGAC GTTGATGGTG    31260
ACGAGGTCTC CTTGGACCTC ATGCCGCAGC TCGATCATGC TTCTCCTAGT ACGGGTTCCG    31320
TTCGACCGAG GCCGACGAAT GAACGCGAGT GACTGTGTCC CTGTGGACGA TTGGGCCGAC    31380
GACCTCCTTC TTGGCCGTGC CGTCAGCGAC GAACCGGGCA GCCAGCAGGT TGTGCTGCCA    31440
GGTCGTCAGG AGTCCGATCT CGCCACCGAA GTTGATCGTG GCGTTGTCGG TGCCGCCCGT    31500
GTACCGGACG GTGTTCTCTT CGACATCGGC GACCTCCTTC ATCAGGTCAA TCGCCATGCG    31560
CCGCAGGCCA ACAGCCTGCA CATCGATCGG TAGCGCCTCA TCACGCGGCA GCGCGATCAC    31620
TACCTGGATC CGATCGGCCA TCAGTGGTAG ATCCCCGGA  CGGTGCGCGA GATGGTGGCG    31680
GGGTTCACGC CGTAGTTGTC GGCGAGATCC TTCTGCTTCA TGCCACCCCG GTACGCCTCC    31740
CGGATGTCCC GGACCTCACG CTCGGTGAGC TTCTGGCGGT TCGGCCGGTT CGGGCCGACC    31800
GGAGCCAAGC TGCCTTTGAC GAACGCTTCA CCGAAGGTCC GCCTCGCGGT GTCGAGCTGA    31860
CTCCGCAGAT CGGCGTTCTC CGACCGCAGG TTCTGGTTCA CAGCCACCTG GCGGTTGACC    31920
GCAGTGACCA ACCGACCGTT CGCGGCGGTC AGGTCTTCGT TCTTCTGGAT CTCCTGCGCC    31980
AGTTCAACCT TGGCGACCCC GAGGTCTCGG GCGAGCTTGG TGTTCGCTTC TCTCAGGTGC    32040
TTCTTCCGCA TCAGCGGCCT CCCTCTCGAC GGAACCGCTC GGTCTCCTCG GCGGTCATGT    32100
AGTAGAAGTC GAGGACGAAG TCCTAGTTGA TGGTTCGGGA CGTGCCGTCT TCGAACGCGA    32160
TGATCAGGAC ACCCTCTTGG GTGTCGAGGA TCGGCTCGCC GTTGAGCACC TTGGTAGCGG    32220
CCGTTGGCGA GGTTGACGAT GGTTGCTCGT TGCGACATGC TCAGCCTCCG TAGCTGTAGG    32280
GTTCGGTGGG GATGTCCTGG TAGGTGTTGG GAGCGATCTC CCGGAGCTGC CGAAGCAATT    32340
CCCCTGCCAG TTCCCGGATT TCGGCATCCG CGGCCTCATG CCAGCGGTTC TTGATGACGT    32400
```

-continued

```
ACCGCCACGC  CCGGTGGTTG  CCCGTGACGA  CCATCGGCGA  GTTGGTCATG  TTCGGCAGAA    32460
CGGCCCGAGC  CGCTTCACGC  GCCTTCTTCC  GGGGGAATCC  GGCATCGCTG  AAGATGTGGA    32520
CGAGGTACTC  GTACGCCTCC  TGGGCGAACG  ACTGAACGTC  CAGCAGGACT  TCCTTGGCCT    32580
TGTCGGCGTC  GGAGCCCGAC  AGCTCCGTAA  ACGCCGGGGG  CACATGGATT  CCCAGCTCCG    32640
TGGGATCGAC  GTACCGCTGC  GACACCACCG  AGAAGCTCAG  GTGCCTGTGA  CGCTCCAGTT    32700
CGGTCAGGAC  CGACCGGCTG  GCCTCGATGT  AGAACGTCGC  GCTGGAATGC  TCCAGCACCG    32760
ACTCATGGCC  CACGTCGAGG  ATGTGGTTGA  GGTAGTCGAC  GTTCTCCCGC  GTCTTGGGGT    32820
TCGGTCGGTC  GAAGCTGAGG  TAGCAGTTCC  GGCCAGCGAA  CTCCGCGAGT  TCGTCTGCCG    32880
ACGTGACGGT  TTCGTCATCA  CCGACGTAGT  CGGTGCCTGC  CCAGCTCGGG  TCTTCGAGGA    32940
TCGTGGATGC  GATCAGTTGG  ACTTTCATAC  TCTCCGCTCA  GAGTTGTGAG  GGGGCCAGTC    33000
GTCGTTGCTG  GCCCCCGGTG  GCTGTCAAGC  GTGGATCAGC  CGTTTTTCTT  GCTGGGGTAC    33060
TGCGCGGGGC  ACTGCTCGTT  GCGAGGAGCG  GTGCAGGAGA  ACAGCGCGTA  GGTGTTCCCC    33120
GCCTTGGAGA  CACCGGACTT  GAACTCCATC  TTGCCGTGCT  TGCAGAACCG  CTCTTCGCCG    33180
CCAGGGGCTT  CCTGCGCCTG  CTGCGGAGCC  CGAGACTGGT  GCTGCTGGCC  ACCGCCGCCG    33240
CTACCGCCGC  CACCGGAGTT  CGGCTTGCTG  CCGCCACCCA  GGTTGGCGAA  GTGATCGGCC    33300
ATCTTGGTCA  CCCGGTCCAT  CAGGGCGAAC  CACTTCTGGC  CCTGGCCCAG  CTTGGCAACC    33360
TCGTCGGGAT  CAACGCCCAG  GTCGACCAGA  GCCTCCGTGA  CGCTGGCGTA  CTTCGGCACC    33420
AGCCACGGCG  CGGAGTAGCT  GCCGTCACCC  TTGAACGTGA  TCGACAACGC  GTCGGCCGGC    33480
GCAGGCCGCA  CCTCCACGGT  CTGGGTCTGC  TGGGCAGGGG  GATCCCAGGG  CGACTCAGTC    33540
GGCGTCTGCT  GCTGCGCTTC  TTCAGCAGGA  GCGGTGTCGA  CCGGCGCGCT  GGCGAACGGG    33600
TCTTCGTAGG  ACAATTGGTT  TCCTCTCACT  TAATGGGGCA  TGCGCCGTTG  GCGCACTCTT    33660
CATCGACACC  GTCAGCGACG  GCTTTGATCG  CAGCAGCCTC  GTACTGCTGC  TTGGTGATTC    33720
GCTCGTAGGG  AGCCTGCGGG  AAGCTCTCCT  CCGGGAAGAT  CGTGGAGCCC  TTGATCAGCC    33780
CAGAGAACCT  CTGCAGATCG  GCGGCGACAT  CCACGCCCTC  GTAGGCGTCC  GGGTCGACGT    33840
TGGCCGTGAA  GCTCACAGCG  TTGTCGGCCC  AGCACGTCTG  GTAGAGCGCC  TGGAACGCCA    33900
GGAGCTGGTG  CAGCGTCAGC  TCGTTGGCTG  ACTCCACGAT  GTCCTCGGCG  TCTCGGCCGA    33960
ACCGTGCGGC  CACGGCCTCG  ACCAAGGTGT  CCTTCGTCGG  GATCTCGACC  ACCCAGGTGT    34020
TGCCTGACTT  GTCGTACTGG  TCCTTCTCGA  CGTGGTACCC  GTCAGCCGCG  TACTGGGACG    34080
CGGTGAGGAA  CTGGTCGTTG  TCCAGCACCG  AGAACCGGAT  GCGCCGGATG  AAGTACCGGG    34140
AGAAGATCGG  GTGGATACCC  TCACTGACTC  CAGGCATCTT  CGCGATGGTC  CCTGTCGGGG    34200
CCACCGTGCG  CTTCTTGACC  GGCACCGGGA  TCCGCAACTC  ATGGCTGAAC  TCCTCGGCCG    34260
CTCTGTCGAC  CTCAGCGGCC  ATCTCCCGCA  AGAAAGCGGT  GAACCGCTTG  TCTCCGGGTG    34320
CCTGCGAATA  CCTTCGGCCT  GTCAGGGCCA  AATAGGAGGC  CACTCCGAGG  TGCCCAACAC    34380
CGATGCGCCG  GTTGCGATCC  AGAACCTCTC  GGCTCTTCGG  ATCAGCGACC  GCTGAGAACG    34440
TCGCCCGGAT  CAGGAACCGC  GTCATCAGAC  GGTGGGCTCG  GATCAGGTCG  ATGTAGTCGG    34500
TCTTCCCGGC  GTCGGTAACG  AACGCCGCGA  GGTTGATGTG  CCCTAGGTTG  CAGGGCTCCC    34560
ACGGCTCCAG  CGTGATCTCT  CCACACGGGT  TGGTGCAGAC  GACCTCGTTG  GGCTCACCGA    34620
CGTTGGACAG  GCTGCTGTCC  CACATCCCCG  GCTCGCCGTT  GCGTACGGCT  CCCTCGGAGA    34680
GAGCCTTCAG  CACCCGGTGT  GCCTTCGTGG  AGCGCGGGTT  GAGCGGGTCG  ACAGGAGCCT    34740
TGGCCAGGCT  CCAGAACGCA  TCGTCCACCT  CGACGGAGAT  GTTCGTGGTC  CAGTGAGATC    34800
```

```
CGCTGTCCTG CTTGATGTTG GTGAACGTCT CGACCTGCCA GTCCGCCCAG TGCATCATCG    34860
CCATGCGAGC CGACCGGCGA ACACCGCCTG CCACCACACA CTGCGCGATG GCGTGGTCGA    34920
TCTCCATCGC ATCGAGACCG GTCAGCGCAC CGCCGTCCTC GAACCTGTAC TGCTCGCCTT    34980
CGCGGGCACA CCGGCTCAGG ATCTCGGAGA CCTCGGTCAG CATCTTCGCC AGAGGCACCG    35040
GCCCAGAGGC CGTGCCGCCG AACGTCTTCA GCTTGCGACC CGCCGCCCGG ACGCGGGACA    35100
CGTCGTAGAC GCGCTCCTTG TGGGCGACAT CATCCCGGTA GTGGGTGTCG ATCAGGTCGA    35160
CCAAGGCGGC TGCCCAGCCC TCGCGGGAGT CCTCGATCAC GAACGCATCG ACCCAGTCAG    35220
AGTCGTAGCG GCTCGACAAC TGACCCGCCT CGGCCAGGTC AGCGTAGTCG TCGTGGTCCT    35280
CGTCGCAGAC GATGTGGACT TCCAGCTCCT GCTTCACGTG CGGGTAGTCA GCGAGGAATC    35340
GGTTCGAGTA GTTCGCCCCG ACGCCACCGC CCTCCATGAG GCGCATGAAC GTGAATTCGA    35400
AGTGGTCCGA GGGCTTCTCG GTCCACCCGC TCACCCAGCA GTTGAACAGG TGCTGGGCGT    35460
TCTTGACGCC CGACGCCCAC AGATGTCGAC CAGCGGGCAG GATCTTGAAC TCCCGCATGA    35520
GTCGGAGCAG ATCTTCTCGC TCTCCTGGGA GCTGATACCG ACTATCAACA AGCGCGAGGT    35580
TCCCAGAAAC CACTCGCTCC ACAGTTTCCG GCCAAGTTTC TCGCGTTCCG TCAGGCTTAA    35640
CCCTGGAGTA CGTCCGATTG TAGACAAGCT CTCCTGTTGG CCCCCAAGGG ATTTCACCCT    35700
CTGTCACTAC TTCCTCTCAG TCAGTTCGTA TGCCTTGAAA TAGGCGTCAG CCGAATCGCC    35760
CTTGGAGAAC GAGACACCGT ACTCATCGCC ACCGATCAGG CCGGTGACAA CGACGCCCTT    35820
CTTGCCCCGG AACCAGCGCC ATGTGCCTCT GGCGGGGTAC TTGGTCTCGT CGCGCTGGAC    35880
GATGACCTTG GTGCCCTTCT TCACGTCGGC CTCCGCTGGC CGTAGCCAGG GGTGAACACG    35940
CCGCCGACGT ACTGCTCCAG GTCGTCCTGC GACCAGTTCT CCAGGAGCAT CGGCTTCTGG    36000
TGTGGGAACA GCTCCGGGAA CACCTCGGCT CGGTACATCT CCGAGCCAGG CATCCCGTTG    36060
AACGTGGGAT CAAGCAGATT TTGCATAGCA CCTCCCTCCC AGGAACTCCG GGATCGGCGG    36120
CTCGTAGAGG TACTCGTCGC GCAGCCCGGG GTGCTCGACC AGCATGATCG CGATGTTCGC    36180
CGTCGGGTCA GAGTGGCCCT CCCCCTGCAC CTTTCGGATG TCAGGGAAGA TGGCGTGCTT    36240
GCTGCCAGGG CCGTCCTTGA CGATGACCTT GCCGTTGTCA TCTCGCTCAA CACCAGCGGT    36300
GATCGCGATG ATGTTGACGT GCTCGGTGAG CGACTTCACG GCTCGCTTCA GCATCGCCTC    36360
GGCAGCCGAA CCCCTCTCCG GGACGACGCC GTCGTCGTAC CGAACCCTGA TCGCCTCTGC    36420
GTGGCGCTCG TTCTTGGAGC CCAGTTCCTT CATCGCCAGC GGCAGGATGT CGACCAGGTA    36480
CCGATTGGTC GACTCACCCC GCAGCGCGTC CTTGACGTTG TCCGACGAGT AGTGGCTGCG    36540
CTCCTGGAAG AGATCCCTGG CCTTGGCCGA GCCCGACAGG ATGTTGTGGA CCTGCTTGCG    36600
GACGTAGATC ACGGCCTCAC CGGGCCGCAG CTCGCCGAGC TTCTTCTGGA TGTACGGACT    36660
TTCGAGGTAC CAGACCCACA GCTCCTGGAC GATCTCGTCC GCTGTCAGGT TGGTCTCCCA    36720
GCCGATCATC GCTTTGCGGG TGGCCCGCAT GAAGAGCTTG TTGATGTCGC CTGTCAAGGC    36780
ATCACCTTCC GTAGGTACTC CTCCCTGTCC AGACGACGGT CGAGGTTGCG GGTGATCTCC    36840
TCGGCGAAGA CCTCACGGAC CTCGCTGGAG CTGATCCGCC GCGACCGTGC GTTCTTGTGC    36900
AGGTACGGCA GCTTGGTGGC TGTCAAGTTT CAGACCTCCC AGACGTGGCC GTCGACCGAG    36960
AATCGGCCTC CGACGATCGG AACCAGCTCG GGCTTGACGT GGTTGCCGTC AACCGTCAAC    37020
AGACCAAACC CGCTCTGCCA GTTGGCCGTT GCACCCTTGA GGTACTGGGC CAGTTTCATG    37080
TTCATCAGGT TGCCGACCTC CATCGACCAC AGCACCTTCT GGTGGCCTCC GTAGCCCCAG    37140
GTGTGGGGCT TGATGCCTTG CCGGTGGGTG TGACCGATGA TCACCGACGT GCCGAACCGC    37200
```

```
TGCATCGCGT TGTACGCGGT GTCAGCCGAC TTCTGCGTCA CCCGGACGCC GCCACGGTGG    37260
CCGTGCGTCG AGATCCAGCC CGGAGCCACC TTGTAGAACT CAGGCAGCAC CGTCACGCCG    37320
AAACCGTCGA AGTCCAAGAG GTTCTCGAAC TTGAACTGGT CGGCGTACTC GACCAGAGCT    37380
GGTGCGAACT TGTGCAGATA GTCGAACGGC CGGCGGTCGT GGTTGCCTTC GTGGACGCCG    37440
ACAGGGCCGT CGTACACGGC CCGCAGCGGG GCCAGGAACC TCGTCTTGGC CTGCTCCGAA    37500
TCGGGCTTGA TCCGCTGGGC GAACTCCTCC GACGAACCCT TGGTCCACCG AGACGGGCTC    37560
GGGTAGTCCA TCAGGTCGCC GATGTGGACG ACCTCGTCGG GCTGGGTGTC GCCGATGAAC    37620
CCGACCACAG CCTTGAGCTG CTTGCGGTCA TCGAACGGGA TCTGCGTGTC GGAGATGACG    37680
ACGATGCGCT TACTCACCCA GTACCTCCAC GAACGGACCC TCGGAGATCT TGGCGTGGTC    37740
GAGCTTGAAA CCGTCGCGGT GCCCCACAG GCGCTCGTTG TAGTCGGGGT ACCGCGACCA     37800
GAACGCGTTG CCCGCGCTCC GCACGGTCTT CACGTCCTTC GGTACGTCGG CCAAGGTGTC    37860
CCACTGGCGA GGTTCGCCCT CGACAGGCTC CTCGTAGATC CGCTCGACGC AACCGGCGTA    37920
ACCGGCCATG TCGGTGAACG AATCACGGTG GTAGCCGGTG CCTTTGACCC TGGCGATCTT    37980
CATCAGGATC ATCAGGTTGG CCACGTCGAT GTCGGAGATC TCCTTCTCCA GGTAGCCCGA    38040
GAACAGCAGG GCGATGTCCT TGAAGTTCTC TCGCGGGTGG CCGTAGTTCT TGTTGCGCTC    38100
ACCGTGGATG AGGCGCTGAG CTTCCTCGAG GATGGATTCA CTCACAGTCC GGTCTCCGAT    38160
GCGGTGTAGT AGTCGATCAA CTCATCGACC TTGTCGGGTT GATAGCCGAT GATCGGCTCG    38220
AAATGGTCGG TCACGATGAC CGGAACCGAG GACGCCTTCA GTACGTCCTG GACGTACGTC    38280
TTGGCCTCGG CGTTGCGCGT CAGGTCGACC ACGTCGTACT CGACCCCAGC GTCGTCCAGG    38340
AACTGCTGGA TCCGGTGGCA CGGGCGGCAA CCCGGCTGGG TGTAGATCGT GATCGGTGTG    38400
AACATCGTTC GCATCAGATC CTTTCCAGCA GAGCGTCTTT GCCCTGCGAT GTGACTAGTG    38460
AGTTGACATC CTCGCCTTCT GGCATGGGGA TGATTCGTGC GTTCGGCAGC GTCTTGGCCA    38520
CCGACTTCGC GAACTCCATA CCGGGCTCGT CGCCGTCAGC CAGGATGTTC ACGTTGCGAT    38580
ACCCGAGGAA CAGCTCGCGG AAGTGCGGCT TCCACATCTG AGCCCCTGGA ACGCCGACCG    38640
TCGGGATCCC GCACAGCTCA GCGGTAATCG CGTCGATCTC ACCTTCGGTG ATCGCCATGT    38700
CCCGCGAGTA GCGGGTCAGT GCGACCGTGT TGTACAGCCG GGGCTTATCC CCCGGCATGG    38760
TCATGTACTT CGGCTTGCCG TCGTCCAGAC GGCGATACCG GATCGCTGCA ACCGACCAGT    38820
TACGCCAGGG CGACCACCGC ATGTACGGGA TCGCCAGGCA GCCTCGGTAC ATCTCATGAC    38880
CAGGGAGTGG ATCTCCCACG AATCCCAGGC CGAACGGTAG AACCTGATGA ACCTGAAGAC    38940
CGCGACTCTC CAAATACTCG GCGGCTGGGC TTCCGTGCAG GCTTCCTCTG TACTGGGATG    39000
TTGCCTCCCA CAGATAGTCC CTCTGCGATT CGGACAGCCT CTGCAAAACT CACCTCCTCT    39060
TCGTGTCGGA TGATCGAGAT CACGTCCCCT CGGACTCCGC AGGCCAGGCA GTTGAACCCT    39120
TGGAGGTCGT AACTGACTGC GGCCGAGGGT GTTTCGTCCC CGTGGAAGGG GCACAGGCAC    39180
TTGTTCCACT CGTAGTGATC CGGTGGAGGA TCCCAGTCCG GGTAGTACCG CTGGATGACC    39240
TCCGCGATGC CGGTGGCTGT CAAGTTTGAC TCCTCAGCTT GTCGGCCTCG ATCGGCGCTA    39300
TGCGCTCCCC GATGACCTGG ACGGCCGGGG GCTTACGCAG GTAGTCGATC GCTCGCTGGA    39360
GCATCTCGAT GCAATCCCGC GCCCAGCCGA GGATGTACTT GTTGCACATC GTGCAGAGCA    39420
GCCCTCGAAC GATGCCCGTC TTGTGGTCAT GGTCTACCGA TAGCCGTTTC CTCTTTCCGT    39480
TCGCCCGCTG GCAGATGTAG CAGCGGCCAC CCTGGAACTC ATAGATGGCC CAGTACTCTT    39540
CAGCGGTGAT GCCGTAGGTG GCCAGGATCC GGGTCTCCCA GCTCGTTGAG CTGCGAGCAG    39600
```

```
CCTTGAACTC  CCGGTGGTGC  GTGGCGCACC  GTGGGCCGGG  ATACTTGGCG  TCCCGTGTGA   39660
GCGGCAACCC  TTGGGCCACA  CAGTCTTTGC  ACGGCTTCCG  TTTGTGCTTA  CGATTCTGCA   39720
CCCGGTACCC  CGGAGTCCTC  TTCGCGGCTC  TCCCCATCGC  TCCCCTTCGG  GTTGTCCATC   39780
AGCAGGCAGA  AGTACGACAG  CACCGCACAC  GCGATGATGT  GTGCGTCGAG  CGCGAACAGC   39840
ACCGGGTTCA  TCCGGCACCT  GTGATGTATC  GCCGTGGGAA  CAGATCCAGC  AGAGCCAGCG   39900
CGATGAGATC  AGCCGCCAGC  TCCGGGTCAG  CCAGCATCCA  TGAGTGGAAG  CCGTCGACTC   39960
CGTAGAAGGA  GGCGTTGGTG  ATCTTGGCCG  TGCTCAGGCC  GGCCTCGTAC  GGAACGATCT   40020
GATCATGCAG  CCCGTGGAGC  ACGGCGGTCG  GTACGCCGTG  GCGGTACATC  GCGTGCAGCA   40080
GCGGTGTCGT  GTCGGCCTTC  ATCAGCGCGA  ACGCAGCGCG  AACGAACCTG  AGCCCGGACA   40140
CCGAATCCCG  CAGCATTCCA  AGGAAGCTCA  GCTTCTCGCC  GGTATCTCGC  AGGTGCATGG   40200
CCTCGTAGCC  GTCGCCGACG  ATGTCGGTCA  CGGCCTCCCC  GAGCTTCTTG  GCAGCTCGGA   40260
ACGCCAGCGT  GGCGTAGTGG  CCCACCTTGA  TGTTGTCGTG  GTGTTCCTGG  CCAGCAGCCG   40320
CGTCCAGCAG  GACCGCTGCC  GCGACTCTGT  GCGGGTGACG  CGCCGCGATT  TCGACCACCA   40380
TGCCGCCCCC  CATCGAGTGG  CCCGCGAAGA  TCGCTCGGTG  GATGTCAAGT  TCGTCCAACG   40440
TCTTGAGGGT  CACGCGGGTC  ATGTCCTCGA  CCGTGTGGCC  GGTCGGCAGT  GAGCCGCTGC   40500
GGCCGTGGTT  GGCCGCGTCG  AGTGCGATGA  CTCGGACCCC  GTGCTCGGCG  AGCCGGGTCA   40560
GCATCTCCTC  GTACGCCTTG  GCGCTCACCG  AGAGCCCGTG  CAGGAACACC  AGCGGGGCGC   40620
CGGTGCCTAC  CGTTGAGACC  CCGACGCGGA  AACCGTCAGC  GAGGACGATG  GTTTCGTGCT   40680
TCATGGCTTG  TCTCCGAAGT  TGATGACAGG  AATGCCAGCC  TTCTGGGCCT  CACGCATGCA   40740
GTGGCGCGTG  CCGACTGACC  TACCGAGAGG  GAACGCCAGG  CAGACATCAG  CCCCAGCCCT   40800
CACCATCTCG  ATGTTGCGGA  GGACGCCAGC  CTTCTTGCCG  TGCCACTCCC  AGTCCGCACG   40860
GTGCAGCTCC  GGGGTGACGT  TGAAGCCTTC  CTGGCGCATC  CCCCAAGCCC  AGCGGTCAGC   40920
GATGTCGTCA  GCGCCGCGAG  CGCCGCCGTG  AACCACCACC  AGGCCATACG  GGACCGGTG    40980
CAGCTCGTCA  GCCAGGGCGT  CCCACACCGT  GGTGCGGTCC  TTCCAGACTC  GCGAGCCGGT   41040
GATCAGTACC  CGACGCATCA  GATCTCCCTC  CAATGCAGCC  CGTCCTCGGA  CTCGACCAAC   41100
TTCGCGCCGT  AGACGCCGTT  GATGATCGCC  AGGTACTCGA  TCTGCTGGGC  CTGCAGAATC   41160
CCGAACGGGC  ATTCGTGAAC  TCCGCTGCGC  GGGTAGCGGA  CTCCGTACTT  CACTTGATCC   41220
ACCTCTTGGC  CAGTCGGTCG  ACGTTCTCCT  CCGAGACGTT  GCGGGCCAGG  CCGGTGACCT   41280
CGCGGCCGTG  GACCTTGGTC  TCGATCACCC  GAGGCTTCTT  CGGATCCGGG  CTCTCCGGGT   41340
CGATCGCCTT  GTGCGTCCAG  ACGGTCGGAC  GCGTCTTGAT  CAGCGCGCCC  AGCACCTGCT   41400
GGTGCAGCGG  GTTGGCCTTG  CGGGGCATGG  CGTTCGGAGT  GGTCATCTGG  GTGTTCCTTT   41460
CGGTGGCTGT  CAAGGGATGG  ATGAAAAGGG  TTGGGGCACA  TGACCGTTTG  TCGTTTAAGC   41520
CAGGGCGGTT  CCCGTGCGCT  CGCCTTACCG  AGCAGACGCG  AGAGCCTAGG  TCACGTACGG   41580
TGACGCCCTG  CGCCCCAAC   CCCCTTGGTC  AACGAAGCTC  GATGTCCGGG  AGGATGGACT   41640
GCGGCTTGAA  GTTGACCTGG  TAGAAGTCGT  CGGAGACGTT  CGCGCCTTCG  ATCTGCTCCA   41700
CGAAGTACGT  GACGTTGTCC  GACAGGCCCA  GGAAGTGCTT  CTTGAACTGG  CCGTTCTGCT   41760
TGCAGGTCAC  GTCCAGCTTC  TGGGCTCCGG  TGTCGGGCTC  GATGGAGCAC  CGACCCTGGA   41820
TCTCCAGCAG  GTACTTATCG  GTGATCCCGT  TGAAGAACAC  GATCCGGCGC  GGGATCTCGA   41880
AGTTGTCAGC  GGCCTTGCTC  AGGTTCTCTG  AGGCCACGTC  GGCGTCGGAG  GTACACCCGA   41940
CCAAGCCCAG  ACCGGCGGCG  AGGGCGATGG  CTGCGGTGGC  GATGGCTTTC  TTCATGTGCG   42000
```

```
CTACTTTCTG   GTTGGTGGCT   GTCAAGTCAG   TGATCGAAGT   CGTTGATCTG   CATGGTGTCT   42060
CCGATGAACT   CCAAGGCGGC   GTAGTCATTC   CCCGACGGAT   CAGACTTGCC   ACCCCGGTTC   42120
TTGACCGTGG   AGACGTTGAG   CGAGTCCGGG   CCGAAGCCGT   CCGACTCGCG   ATGGAGCGTG   42180
AGGACCATCT   CGGGCACACG   CCCGATCTGA   CCCTTGATCC   CTCCTAGCGG   GATCGCTTTG   42240
TCGCCGTCGT   TGTACGGGCC   GGTGACGTGG   TGGAGCCCGA   TCACGCAAGA   GCCAGTCTCC   42300
CTGGCCATTT   CGTGCAGGTA   GTCCATCAGC   GACTCCAGGC   CGCTGAACGG   GTCATCCCCG   42360
TCCCCCGACT   CGGTGCGGAC   GTTGGTGATG   TTGTCCACGA   CGATCAGCGC   AGGGAAGTCC   42420
TCGTAGAGCG   CGTCGTACGC   TGCGAGGGCG   TTCTCGATCT   CGTCCAACGA   CGGAGATGCC   42480
TTGTAGTTGA   ACCGGATCGG   GATCTCATCG   AGGTCGTTGG   CAATCGACTC   CTCGATGCTC   42540
TGTTCCCGGA   CTGCCCGCGT   CGATCGCTCG   AGCGACCATC   CGCTCAGGAT   GGAGACTGAC   42600
CGCGAGATCT   GGGTGAACGC   GTCGGAGTCC   GCCGAGAAGT   ACAGCGTCGG   TACCTTCGAC   42660
TTCAGCGCGT   AAGCCAGGAC   AAAAGCCGAT   TTACCAGTGC   CAGGACCGGC   GCATACAAGG   42720
ACCAACTGAC   CTCGTCGTAG   ACGAGTCCCC   TTCTGATCAA   GTGCGTTCCA   CACCGTTGGG   42780
AGTGGGTCAC   CCGCGTTCCC   TCGGATGTAC   AGGCTCTGCC   TCGGTGTGTA   CAGCGTCCTC   42840
CTCCTTTTCT   CGTTCGAGCA   TCTCCCGGAG   CATCCAACCG   GGGATGACGT   TGTTGAAGCT   42900
CACAGACCCT   CCTCGATGTC   GTTGACCATC   TCGCGGACCT   CGTCCATCGG   CACCAGGTCG   42960
TGCCAGGCGT   CCAGCCCGAC   GTGGATCTGC   CGTGGGTTGG   TCATGGTCGA   CCGAATGATC   43020
CGGGAGTGCG   TGTGGCCGTG   CAGTAGGATC   AATCCTTCAT   CCCGCAGCCG   CCACTGCGTG   43080
AAGCGTTGCT   CGGCGGTGTG   GTCGCCGACG   TACGGGAAGT   GGCTCAGCAG   CACGTTGGTG   43140
TGACCGCCTC   CGTCGAGGGG   GACGCGAAGC   CTCGCGGCCG   TCGACATGTA   ATCGAGCACG   43200
TTCCAGTACA   GCCGGGACAG   CCGGGGAGCG   TCCCGGTACA   TCGGGTGAGG   CCGATCATGG   43260
TTGCCCAGGA   TCAGCCGCTT   GCGGCCTGGC   CGGTTCAGCA   GCCAGCCCAG   AGCATCGAGC   43320
TGCGCTCGGG   TGCCGCCTGA   GCTGATGTCC   CCCAGGATCC   AGACCACATC   TTCCTTGCCG   43380
ACCTGTTCGT   CCCACAGCTC   CGCGAGGTGG   AGGTCGTGGT   CCGGGCCAGC   CCAGTCTCGG   43440
TCCTCCGCTA   CCTTGGCGTG   GCCGATGTGT   AGGTCGGAGG   TGAACCAGAC   GTTGCTCACG   43500
CTGGCTCCCT   CACGTCGGGC   CGACCGTGGG   TCTGCCAGAT   GAACTCTTCG   ATCTGGTCGA   43560
CCGCGATGAA   GAGGTCATCC   CCGTCGATCT   TCGTCGGGAG   CCCCATCAGG   ATCGCCAGGA   43620
TCTTGTCTCG   GATCACTGCT   TGACCACCCC   CGCGTCATGG   ATCGGCCGGC   CAGCTCGGTG   43680
CGCCGCCTGC   TCCGCGTCCA   TCGCTCGCTG   GATCTGGTTC   ATCAGTTGGG   TGCCTCGAAG   43740
CTTCAGCAGC   TTCATGGTGT   GAGCACCCTT   GAATCCGACG   CGGTGCATCC   GCAGGACCGC   43800
CGCCGTCTCA   TGCGGCGCGT   ACGGCGACTT   CAGCTTCGGG   TCGTTGGGAT   CCCAATCCTT   43860
CTTCATGCCT   TCTCCTCTTG   GTGGCTGTCA   AGTTCGATGA   CGATGTTCAC   GCGACCCACT   43920
CCTTGCCGTT   CCACCGCCGA   CCATCTGGGT   AGGCGATGAT   GACTTCCCGG   TCGGGCCGCT   43980
CCTCGCTGTG   AGCGCGAGCG   AACGGAACG    CCGCTTCTGG   CGTCGGGAAC   GGCCAGCGCG   44040
AGGGCTGGGC   CGACTGGTGC   CACTTCGGCA   TGTCTGGGAT   CGGACCCAGC   TCCACGTAGG   44100
TGTAGCTCGT   CCCGGTGCTG   AGATCGAGCG   TCTTCCGGTA   TTCCTTCATG   CCTGCCTTAA   44160
TGGGGAAGGA   GTCTGCGGGT   GGCTGTCAAG   TTGCGATCAC   TTAAAAACGG   GGCAACTGTA   44220
GGACACATCA   CAGAATTTGC   ATTTGTCCGG   TTCCGGCAAC   GGGTCGAACA   TCGAGGCTGC   44280
GATGCCTTCC   TCGACCCTGT   GGAACTCCTC   GGTGATGGCT   TCACGCGTCC   ACTTCGTCAG   44340
GTCGTAGGGC   TTGGTCGGCT   TCGGTGCCTT   GCCCTTCTTC   CCCACCATGA   AGTAGTCGCC   44400
```

```
GGTCTTCGGA  GCCTCGACAC  CGTAAGTCAT  CGCGACCGCG  AGCGCGTACA  CGCCGAGCTG   44460
GAAGTCGTCT  CCCGGTTGGT  TCCCGGTCTT  GTAGTCCCGG  ACTCGAAGCT  CCCCGTCGAC   44520
CACGACGACG  GCGTCGATGT  ATCCGCGAAC  CAGGATCCCG  TCGAGTTCGA  TTTCGAAGTA   44580
CAGCTCGATC  GCTGGCGTAC  CGTCCGGGGT  CACCCAGATC  TCCTGGCCGG  GAGTCCCCCG   44640
CCACGCGAAG  AACTTCTCGA  CCTGCTCCAG  GCCGACGGTG  TACCGGCGCT  CGATGTCTCG   44700
CTGGCCGTTG  TACGGACCTG  ACCACGTCCA  CCACTCGAAG  TTCGGGGTCT  CCTCGGTGAA   44760
GGCTCCAACG  TCGTTGGCGT  AGTGCCAGCG  GAACATGTCC  TTGGCCTCGT  CAAGCGTAAG   44820
CGGCATGCCG  TAGGACTCCC  ATACCTCGAC  CGCCTCGGCG  ACAGCGTGGA  ACGCGGTCCC   44880
CTGCGGCAGC  CAGGCCGCTG  GCCGCTGCCA  CACCTTGTCG  ATCCGAGCGA  GCTTGTACGC   44940
CATCGGGCAC  TTCGTGTACT  GGTTGATCTG  GCTCACCGAG  CGCAGCGGAA  GCTTGATCTG   45000
CGTCACGGCG  CGGCCATTTC  GCCGTTGCCG  GTCAACGCGG  TCTCCACCGT  CGAGCCCACG   45060
ACCTCTCGGA  TCTCATCCAG  CGATGGGCAC  ATCGGGGACT  CAACGAAACT  GTGTGGCCTC   45120
AGCCTGGCTA  CCAAGAACTC  TCCTCTCCCG  TGCATCATGT  TGTCGTCATG  CCGGAAGCCA   45180
CGTGCGAGCA  CGTCAACCTG  GTCGGCCTTC  AGAATCTCCT  CGGCGACAGG  CCGATACATC   45240
GGCTTCGTGT  CTCGGCACAG  CGGGCTCCGG  TACGCGAGCA  GCAGGGTGAC  AACCTGGGAA   45300
GGATCGTCCT  CCATCCAAGC  CTTGCACTTC  CATGCTTCCA  GCCACCCGTG  ACGCTCGACC   45360
AGCTTCTCTG  GCTGCGTGTA  AACGACCCCC  TCGAACTGGC  CTACAAGGCT  AGTGAGCGGC   45420
ATTGCGGTTC  CTTACTGCGT  GGGCTCCGCT  GGCTACGGAG  AACGCACGCG  CGTCGTGTTA   45480
GTTCAGGAGT  TCCTCGATGT  CGGGTGGCCA  GCACCAGATC  ATCTCTCCCT  CGTCTGTCAA   45540
GTTGGTGTAC  TCGTTGACCC  GGATCAACAG  GTCGTCGTCC  TCGATGGTTC  TCGGGACGTA   45600
CCTGAAGCCT  CCACCGGCCA  TGCCGGGGTA  GGGCTCAATG  TTGGGGTCGA  ACTCGACTAC   45660
CACATCGTTG  TCGCGCAGCA  TCTTCCACCA  CGACAACAGG  CGCTTCCGCT  TGTCCTCTGA   45720
CATCGTCTTG  AAGCTGCCCA  CGCGCATGTA  CTCACCGTGG  TCACGAAGTC  TCTGGTAGGC   45780
CTTGGACTTC  CCCTGAAACT  TCGTCGTCTG  CCACGGCCAG  GCCAGCGTGG  ACGTTCTTCT   45840
TGCCTTCACG  GCGCACACGC  TCACGGCCGG  CCGGCCTCAC  CACACCTTTC  GCGTGGGCCA   45900
GCAGAACGTG  GCCGCTGCGG  TGGATGACTC  GACCCTTGAA  GTCGCCTTCC  AAGGCTTGGA   45960
CGGAGTACCA  CGGCTTGCCC  TCACGGTGCG  TGAAGTGCAG  GTTCTTGTAG  ACGAAGACGC   46020
GAATTGGCTT  GGGGTTCATG  CGATCCAGTC  ATCCAGGTAG  TTGTCTTTGA  CGCTGAAGCG   46080
TCGGGTCCGA  CTCAAGACTT  CGATGGCCGC  GAGGATCTCG  CGGTCCTCGC  CTTCGCGCTC   46140
CATCGCTTCG  TCTTCGACGT  TGATCACTTC  GATCCCTTCG  GCTTGGCAGG  CGGTGTCTTC   46200
CAGGGGTTCA  TGCCCAGCCG  CCGAGCGCGG  CGCATGGCAA  CCATGATCTC  GACGTTCATG   46260
AGGCCGAAAC  CTCCCACGTA  CCAACGGCTT  CGCCGCGAAG  GTAGATGTGA  CCTCCATCGC   46320
CGAGCTGGTC  GATGACCAGG  CCGTTGCGCG  AAGCGGCAGC  TTCGAGGTGG  TCGATGAGGA   46380
TCTGGCGATG  GCTCGCCGAT  ACCTTCGTAT  TCTTGCCGTC  GCGGTCACGG  GTGGCAGTCA   46440
AGGTGAACAC  AGGTCAGGTA  CCTCTCAGTA  GTCGGAGTGC  TGGAGTTCGA  AGCCTTCGAG   46500
GTCACCGACC  TCGTCGTCCC  ACGCGGACGG  GTTGCCGCGC  CAGTCGTCGC  GAAGCCTCTG   46560
GCCGCTGGCG  TTGTAGCAGG  CACCGCAGTT  GCGACAGTCC  ACGTCGCTCT  GGCCTCGGTA   46620
CCTCTGCGCC  TCATGGCCGC  ACCGTGAGCA  GTCCACGCG  GCGTAATCGC  CGTCGATGAT   46680
GAACCCTTCG  GCGTCACGCA  CAGCTTCGAC  GTAGCGGTAG  TTGTTGGCCA  TGATCAGCTC   46740
CCCAGCTCGT  TGGCGATGGC  TTGGTGGGCA  GCCTCACGGA  AGGTCAGCCC  GTCGTCGTAC   46800
```

```
GCGTCGTGGT AGGTCCAGTC CGCGATGTCT CGTCGGCCGA CCCCGAACGT CTCTTGCATG    46860
TAGGCGTCCA GGTTGGCCAT CCACAGGTGG AAGCTCACAG CTACCTCACT TCTTGGTGGT    46920
GGAGAACAGA ACGCTCTTGC GTCCGTTGAT GCACAGACCG CACCTAGCGC AGGCCGATCC    46980
CTTGGCGTTG ATCAGGTCGA AGTCTCGGTT GTTCAGCTCC GGGCAGCGCA CGGCCGTCGG    47040
GAACTGTGCC TTGCCTTCGG CGAACGTCGT GTCGACGTAG GCGATGTTGA TGCCCTTGCC    47100
TTCCAGGAAC CGGGCCACGT CTACGTTGTC GGGATCCGCG CTGAAGTACA GCGACAGGTT    47160
CGACAGCTTC TGTGCGTGCA GGTAGACCGC TGCGGTCTGA ACCCTGGTGT AGGCCCAGAA    47220
CTGCACGTCG CTGAAGTCTC GGATGACACG CGCCCACGCT GCGACGTAGG TCGGGCTGAA    47280
GAAGTCGCCA TCCCAGTGGA TACGGAACAG CTTCGGAGCC TTCTTCTTGT CGCAATCCTT    47340
GACGAAGTCT GCCATCATCT CGGACAGCAG GGTCACGGTG TCTGTCAAGT CAGCGTCACG    47400
CAACAGCTCC CAGTTGTGCA GCAGCACACT GCTCACGGCT TTGCGGACCT TCTCCAGCTT    47460
GCCCGCGTAG CACACCTTGG CACAGAACGC GGTCGCGTCC GGGCAGGAGA ACCCTTGCCC    47520
ACTGGGCAGA CCGATGCTGT TCGCGATGCC TACGGTGGCG TTGCCGCCTT TGGTGACGTG    47580
GACGTAGTTG GTGACTTTGC GGTCGTTCGA TCGCTTCAGC GATGCCATGT CTAGAACCCT    47640
TCGGTGGCTG TCAAGTCAGC GGACGCGAAT GATGTTGGTG CCTCGGCAGA CGTAGATCTT    47700
GCCGTCGATG TACACCTTGC GCTCGGAGGA CATAGTGAAT CCTTTCTCGG TGGCTGTCAA    47760
GTCTCAGGCC CAGCGACGTT TCGTCGGCCG GGGGTGGCGA ACCTTCGGAG CGTTCTTACG    47820
CGGTGCCTTG CGGATGACGG TGTCGCCAGT GATCGTGATG TCTTCGACCA GGGCAGCCTC    47880
ACGCTCTGCA GCGATCTCGG AGGTCGGGAC GTTGACCACT TCCGGCTTGT TGCTGAAGTC    47940
AGTCCACCCC TTGGTGCCCT TCTCCAGCTC AGCGTCGACG GTGCGAACCG TCGACAGCTC    48000
AGGTGCGACG AACGGTGTCT TGATGGACTC GCGTGCCGTG ACGCGAACCT CGCGGTGCTC    48060
GGTGAAGACG GACATAGCTC ACCCCTTCCG GTAGCTGTCA AGTCAAGAAT CAAAGCTCAG    48120
GTAGTGGGTA GCCAGGAATC GAACCTGGTA GTCGTGATGC CGCGATACCA AAGCTCAGGT    48180
ATCCGCCAGA CCATAGCTCA GCGATCATTC CATCGCGCCA GAGCTACCCG GTAGTCTTTT    48240
GTTCTCCCCG TGGGTCAACA GAATCTATCG GATCCTCGCC ACAGGTCTAC ATTCAGTTAT    48300
CCGCAGTGTC CGCACTTTAT CGGCATCGGA CTTCCGCCTC ACCCGCGAAT GCTGTCGAAG    48360
CCATTCGCGA ATGTTGGGTC GGGCTGCGGC CCTTCCCGGT CTTGCGTGAT TCTCACTCTA    48420
CCGGACTAGT CGGTGGCTGT CAAGCGGGCC GTTTTGGTAT CGGCATCGAT GCCCTCGTTT    48480
AGCGCCGCTG GCATAAGGCG CTACCCGCTC GACTCACCGG TCCAAGTTGG TGATGACATT    48540
CACTCTAGCG TATCGCTCGG TGGCTGTCAA CCGGAGAATC ACACCGGATT TTCACCGGAT    48600
CCGGCGCGAT CGTTTCCGAT CCGCCTATCG CGTCGTGCTT GCTGCGATGA CACAAGTAAA    48660
CACCACGGCC GGGTAGCTGT CAAGCCCGAA TTGCAAATTG GTGTGTGACG TGCGGTTACG    48720
CCGCTGTCCG GGTGGCTGTA AAGGGCACGT AGGGCACGTG TGGCAGGCCA GACGCAACCC    48780
ACTAGCGGCC GGTAGCCGCG TGCATAGGCT GCTCGTTATG TGCCCGGTAT GGGTGCTGTG    48840
AGCTGCACAA TCGCGGGCTG TCGGGCTGTC GTCACGCTGT CGCTGTCGTC GCCGGGTGGC    48900
TGTCCAGTCG CCCACCGAAA TAAGCGAAAT AAGCACCGTC GTCGCAGGTC CATAGGCTGC    48960
TCACTATCGC ATCGGTATGC CCTTGCACAC GTGTGTGAGC TGGTCACGTG CTGGTGTGGT    49020
GTGCCGTGTG CGCTGGTGTG TATGCGCTGG TCAGCGTATG GGCACAGTGT GCGTGTGAGT    49080
TAGCTGTGAG CTGAGGCCGG CATTCGCATC GTCGCAGGTC AGCACGCGTA TGCGTGCATG    49140
TGTCCTCGGT TGCTGGGCAT CGTGTGCCCC TCGAGGCACG CGTGCCGTGA GCGTTTGCTG    49200
```

```
TGCATGCCAT  CGTCGCAGGT  CACGGGGGGT  AGGGGGGTTC  CCCCCAGGGG  CGCCTTCCTG      49260
ACCGGTCGGT  TA                                                              49272
```